(12) United States Patent
Nakatani et al.

(10) Patent No.: US 8,202,439 B2
(45) Date of Patent: *Jun. 19, 2012

(54) DIAPHRAGM AND DEVICE FOR MEASURING CELLULAR POTENTIAL USING THE SAME, MANUFACTURING METHOD OF THE DIAPHRAGM

(75) Inventors: Masaya Nakatani, Osaka (JP); Soichiro Hiraoka, Osaka (JP); Hiroshi Ushio, Osaka (JP); Akiyoshi Oshima, Osaka (JP); Hiroaki Oka, Osaka (JP); Fumiaki Emoto, Ehime (JP)

(73) Assignee: Panasonic Corporation, Osaka (JP)

( * ) Notice: Subject to any disclaimer, the term of this patent is extended or adjusted under 35 U.S.C. 154(b) by 576 days.
This patent is subject to a terminal disclaimer.

(21) Appl. No.: 12/359,426
(22) Filed: Jan. 26, 2009
(65) Prior Publication Data

US 2009/0239033 A1    Sep. 24, 2009

Related U.S. Application Data

(60) Continuation-in-part of application No. 10/485,644, filed as application No. PCT/JP2003/006920 on Jun. 2, (Continued)

(30) Foreign Application Priority Data

| Jun. 5, 2002 | (JP) | 2002-163934 |
|---|---|---|
| Aug. 1, 2002 | (JP) | 2002-224563 |
| Mar. 7, 2003 | (JP) | 2003-062228 |
| Mar. 7, 2003 | (JP) | 2003-062229 |
| Nov. 21, 2003 | (JP) | 2003-392220 |
| Mar. 22, 2004 | (JP) | 2004-082240 |
| Aug. 25, 2004 | (JP) | 2004-245574 |
| Nov. 8, 2004 | (JP) | 2004-323358 |
| Jun. 7, 2005 | (JP) | 2005-166492 |
| Jun. 29, 2005 | (JP) | 2005-190210 |
| Jun. 29, 2005 | (JP) | 2005-190211 |
| Jun. 29, 2005 | (JP) | 2005-190212 |
| Jun. 29, 2005 | (JP) | 2005-190213 |
| Dec. 20, 2005 | (JP) | 2005-366060 |
| May 17, 2006 | (JP) | 2006-137538 |
| May 17, 2006 | (JP) | 2006-137540 |
| May 25, 2006 | (JP) | 2006-144801 |
| Jan. 31, 2007 | (JP) | 2007-020834 |
| Sep. 11, 2007 | (JP) | 2007-234935 |
| Sep. 21, 2007 | (JP) | 2007-244829 |
| Oct. 15, 2007 | (JP) | 2007-267596 |

(51) Int. Cl.
*B44C 1/22* (2006.01)
*H01L 21/302* (2006.01)

(52) U.S. Cl. ........... 216/41; 216/17; 216/56; 216/58; 438/733; 438/734

(58) Field of Classification Search .......... 216/17, 216/41, 56, 58; 438/733, 734
See application file for complete search history.

(56) References Cited

U.S. PATENT DOCUMENTS
2,366,654 A    1/1945 Rotter et al.
(Continued)

FOREIGN PATENT DOCUMENTS
EP    0 652 308 A2    5/1995
(Continued)

OTHER PUBLICATIONS
Machine English translation of JP 2002-96472.*
(Continued)

*Primary Examiner* — Shamim Ahmed
(74) *Attorney, Agent, or Firm* — RatnerPrestia

(57) ABSTRACT

A diaphragm is formed by etching a substrate. This substrate has a first surface provided with a depression by isotropic dry etching, and a second surface opposite the first surface. Furthermore, a through-hole is formed from the depression to the second surface by anisotropic dry etching. The depression and the through-hole are formed by using one resist mask. The depression has a hemispherical shape or a semi-elliptical spherical shape.

8 Claims, 16 Drawing Sheets

Related U.S. Application Data 2003, now Pat. No. 7,501,278, and a continuation-in-part of application No. 10/513,392, filed as application No. PCT/JP2004/002951 on Mar. 8, 2004, and a continuation-in-part of application No. 11/081,759, filed on Mar. 17, 2005, and a continuation-in-part of application No. 10/595,275, filed as application No. PCT/JP2005/013029 on Jul. 14, 2005, and a continuation-in-part of application No. 11/915,172, filed as application No. PCT/JP2006/310846 on May 31, 2006, and a continuation-in-part of application No. 11/719,610, filed as application No. PCT/JP2006/325217 on Dec. 19, 2006, and a continuation-in-part of application No. 11/916,947, filed as application No. PCT/JP2006/313359 on Jun. 28, 2006, and a continuation-in-part of application No. 11/914,283, filed as application No. PCT/JP2007/060326 on May 21, 2007, and a continuation-in-part of application No. 11/913,116, filed as application No. PCT/JP2007/059743 on May 11, 2007, which is a continuation-in-part of application No. PCT/JP2008/002430, filed on Sep. 4, 2008, and a continuation-in-part of application No. 12/133,432, filed on Jun. 5, 2008, which is a division of application No. 10/991,269, filed on Nov. 17, 2004, now Pat. No. 7,396,673.

(56) References Cited

U.S. PATENT DOCUMENTS

| | | | |
|---|---|---|---|
| 4,495,220 A * | 1/1985 | Wolf et al. | 438/623 |
| 4,704,255 A | 11/1987 | Jolley | |
| 4,937,226 A * | 6/1990 | Nishiguchi | 505/413 |
| 5,183,744 A | 2/1993 | Kawamura et al. | |
| 5,204,690 A * | 4/1993 | Lorenze et al. | 347/93 |
| 5,413,139 A * | 5/1995 | Kusumoto et al. | 137/341 |
| 5,569,591 A | 10/1996 | Kell et al. | |
| 5,690,841 A * | 11/1997 | Elderstig | 216/39 |
| 5,893,757 A | 4/1999 | Su et al. | |
| 6,051,422 A | 4/2000 | Kovacs et al. | |
| 6,063,260 A | 5/2000 | Olesen et al. | |
| 6,163,719 A | 12/2000 | Sherman | |
| 6,315,940 B1 | 11/2001 | Nisch et al. | |
| 6,413,792 B1 | 7/2002 | Sauer et al. | |
| 6,488,829 B1 | 12/2002 | Schroeder et al. | |
| 6,627,067 B1 | 9/2003 | Branton et al. | |
| 6,682,649 B1 | 1/2004 | Petersen et al. | |
| 6,699,697 B2 | 3/2004 | Kiemic et al. | |
| 6,758,961 B1 | 7/2004 | Vogel et al. | |
| 6,776,896 B1 | 8/2004 | Osipchuk | |
| 6,932,893 B2 | 8/2005 | Bech et al. | |
| 6,936,462 B1 | 8/2005 | Owen et al. | |
| 6,984,297 B2 | 1/2006 | Nisch et al. | |
| 7,006,929 B2 | 2/2006 | Oka et al. | |
| 7,683,374 B2 | 3/2010 | Lin et al. | |
| 2001/0003678 A1 * | 6/2001 | Stinnett et al. | 438/723 |
| 2001/0046706 A1 | 11/2001 | Rubinsky | |
| 2002/0056698 A1 * | 5/2002 | Makigaki et al. | 216/27 |
| 2002/0063067 A1 | 5/2002 | Bech et al. | |
| 2002/0064841 A1 | 5/2002 | Kiemic et al. | |
| 2002/0074227 A1 | 6/2002 | Nisch et al. | |
| 2002/0104757 A1 | 8/2002 | Schmidt | |
| 2002/0144905 A1 | 10/2002 | Schmidt | |
| 2002/0182627 A1 | 12/2002 | Wang et al. | |
| 2003/0032946 A1 | 2/2003 | Fishman et al. | |
| 2003/0052002 A1 | 3/2003 | Vogel et al. | |
| 2003/0058309 A1 * | 3/2003 | Haluzak et al. | 347/65 |
| 2003/0080314 A1 | 5/2003 | Nisch et al. | |
| 2003/0107386 A1 | 6/2003 | Dodgson et al. | |
| 2003/0113833 A1 | 6/2003 | Oka et al. | |
| 2003/0153067 A1 | 8/2003 | Stett et al. | |
| 2003/0194808 A1 | 10/2003 | Rubinsky et al. | |
| 2004/0011651 A1 | 1/2004 | Becker et al. | |
| 2004/0033483 A1 | 2/2004 | Oka et al. | |
| 2004/0055901 A1 | 3/2004 | Petersen et al. | |
| 2004/0146849 A1 | 7/2004 | Huang et al. | |
| 2004/0152067 A1 | 8/2004 | Wang et al. | |
| 2004/0175844 A1 | 9/2004 | Yang et al. | |
| 2004/0197898 A1 | 10/2004 | Nakatani et al. | |
| 2004/0214312 A1 | 10/2004 | Tyvoll et al. | |
| 2005/0112756 A1 | 5/2005 | Nakatani et al. | |
| 2005/0158845 A1 | 7/2005 | Wikswo et al. | |
| 2005/0196746 A1 | 9/2005 | Xu et al. | |
| 2005/0214740 A1 | 9/2005 | Ushio et al. | |
| 2005/0221469 A1 | 10/2005 | Nakatani et al. | |
| 2006/0159916 A1 | 7/2006 | Dubrow et al. | |
| 2006/0163063 A1 | 7/2006 | Picollet-Dahan et al. | |
| 2006/0228771 A1 | 10/2006 | Dodgson et al. | |

FOREIGN PATENT DOCUMENTS

| | | |
|---|---|---|
| EP | 0 689 051 A2 | 12/1995 |
| EP | 1 203 823 | 5/2002 |
| EP | 1 352 952 A1 | 10/2003 |
| EP | 1 533 615 A2 | 5/2005 |
| FR | 2844052 A1 | 3/2004 |
| JP | 02-131569 | 5/1990 |
| JP | 2-131569 | 5/1990 |
| JP | 06-244257 A | 9/1994 |
| JP | 6-244275 A | 9/1994 |
| JP | 7-201509 A | 8/1995 |
| JP | 09-211010 | 8/1997 |
| JP | 09-289886 | 11/1997 |
| JP | 2000-243700 A | 9/2000 |
| JP | 2002-508516 | 3/2002 |
| JP | 2002-096472 A * | 4/2002 |
| JP | 2002-518678 | 6/2002 |
| JP | 2002-518678 A | 6/2002 |
| JP | 2003-511668 | 3/2003 |
| JP | 2003-527581 | 9/2003 |
| JP | 3486171 B | 10/2003 |
| JP | 2004-000163 | 1/2004 |
| JP | 2004-012215 A | 1/2004 |
| JP | 2004-069309 | 3/2004 |
| JP | 2004-271330 A | 9/2004 |
| JP | 2004-271331 A | 9/2004 |
| JP | 2004-333485 A | 11/2004 |
| JP | 2005-156234 | 6/2005 |
| JP | 2007-515299 T | 6/2007 |
| WO | WO 99/31503 | 6/1999 |
| WO | WO 99/32881 | 7/1999 |
| WO | WO 99/66329 | 12/1999 |
| WO | WO 00/34776 | 6/2000 |
| WO | WO 01/25769 A2 | 4/2001 |
| WO | WO 01/27614 A1 | 4/2001 |
| WO | WO 01/48474 | 7/2001 |
| WO | WO 02/03058 | 1/2002 |
| WO | WO 02/29402 A | 4/2002 |
| WO | WO 02/055653 A1 | 7/2002 |
| WO | WO 02/065092 A2 | 8/2002 |
| WO | WO 02/099408 A1 | 12/2002 |
| WO | WO 02/103354 A | 12/2002 |
| WO | WO 03-016555 | 2/2003 |
| WO | WO 03/016555 A1 | 2/2003 |
| WO | 2003-511699 A | 3/2003 |
| WO | WO2004/038410 A1 | 5/2004 |
| WO | WO 2004/079354 A1 | 9/2004 |
| WO | WO 2004/099068 A2 | 11/2004 |
| WO | WO 2006/022092 A1 | 3/2006 |
| WO | WO 2007/046432 A | 4/2007 |

OTHER PUBLICATIONS

International Search Report for Application No. PCT/JP2006/310846, filed Sep. 19, 2006.

Suzuki, K. et al., "The Electrophysiological Biosensor for Batch-Measurement of Cell Signals," IEEJ Trans. SM, vol. 125, No. 5, 2005, pp. 216-221.

International Search Report for corresponding PCT International Application No. PCT/JP06/325217 dated Jan. 23, 2007.

English Translation of PCT/ISA/210.

Japanese Search Report for Application No. PCT/JP2007/060326, dated Aug. 28, 2007.

English translation of Form PCT/ISA/210.

T. Sordel et al.; "A Silicon-Based Multi-Patch Device: Application for Ionic Currents Sensing on Single Cells"; 8$^{th}$ International Conference on Miniaturized Systems for Chemistry and Life Sciences Sep. 26-30, 2004, Malmo, Sweden, pp. 521-522; CEA Grenoble, Life Science Division, Grenoble, France.

Japanese language International Search Report for PCT/JP2007/059743, dated Jun. 26, 2007.

Partial European Search Report for EP 04 02 7447, dated Feb. 17, 2005.

European Search Report for EP 04 02 7447, dated Apr. 13, 2005.

European Search Report for Application No. EP 07 11 6970 dated Nov. 2, 2007.

European Search Report for Application No. EP 07 11 6972 dated Nov. 15, 2007.

M. Watanabe et al., "Trial Micro-Channel Array for Cell Activity Analysis," Dai 6 Kai Chino Mechatronics Workshop-Ningen o Shien suru Mechatronics Gijutsu-Koen Ronbunshu, Aug. 30, 2001, pp. 247-261 (with English translation).

Taylor, G.I., "The Criterion for Turbulence in Curved Pipes," Proceedings of the Royal Society of London, Series A. Containing Papers of a Mathematical and Physical Character (1905-1934), vol. 124, #794, pp. 243-249. Royal Society Publishing, Jun. 4, 1929.

Wolf, Julie B. "Transformation of *E. coli* by Electroporation." Jan. 17, 2006. <http://userpages.umbc.edu/-jwolf/m7.htm>.

Klemic, et al., "Micromolded PDMS planar electrode allows patch clamp electrical recordings from cells," Biosensors and Bioelectronics, vol. 17, (2002), pp. 597-604.

Neher, et al., "Single-channel currents recorded from membrane of denervated frog muscle fibres," Nature 260 (1976), pp. 799-802.

Hamill et al., "Improved Patch-Clamp Techniques for High-Resolution Current Recording from Cells and Cell-Free Membrane Patches," Pflubers Archiv 391 (1981), pp. 85-100.

US Office Action for U.S. Appl. No. 12/245,091, Nov. 9, 2010, Panasonic Corporation.

US Office Action for U.S. Appl. No. 11/913,116, Nov. 17, 2010, Panasonic Corporation.

US Office Action for U.S. Appl. No. 11/913,116, May 23, 2011, Panasonic Corporation.

Japanese Office Action for Application No. 2010-186807, Mar. 29, 2011, Panasonic Corporation.

Supplementary European Search Report for EP 05 76 5636 dated Jan. 23, 2012.

* cited by examiner

DIAPHRAGM AND DEVICE FOR MEASURING CELLULAR POTENTIAL USING THE SAME, MANUFACTURING METHOD OF THE DIAPHRAGM

This application is a continuation in part of
1) U.S. Pat. No. 7,501,278 application Ser. No. 10/485,644, filed Feb. 3, 2004, which is a National Phase of PCT/JP2003/06920, filed Jun. 2, 2003;
2) U.S. patent application Ser. No. 10/513,392, filed Nov. 4, 2004, which is a National Phase of PCT/JP2004/02951, filed Mar. 8, 2004, (pending);
3) U.S. patent application Ser. No. 11/081,759, filed Mar. 17, 2005;
4) U.S. patent application Ser. No. 10/595,275, filed Apr. 4, 2006, which is a National Phase of PCT/JP2005/13029, filed Jul. 14, 2005;
5) U.S. patent application Ser. No. 11/915,172, filed Nov. 21, 2007, which is a National Phase of PCT/JP2006/310846, filed May 31, 2006;
6) U.S. patent application Ser. No. 11/719,610, filed May 17, 2007, which is a National Phase of PCT/JP2006/325217, filed Dec. 19, 2006;
7) U.S. patent application Ser. No. 11/916,947, filed Dec. 7, 2007, which is a National Phase of PCT/JP2006/313359, filed Jun. 28, 2006;
8) U.S. patent application Ser. No. 11/914,283, filed Nov. 13, 2007, which is a National Phase of PCT/JP2007/060326, filed May 21, 2007;
9) U.S. patent application Ser. No. 11/913,116, filed Oct. 30, 2007, which is a National Phase of PCT/JP2007/059743, filed May 11, 2007;
10) PCT International Application PCT/JP2008/002430, filed Sep. 4, 2008;
11) U.S. patent application Ser. No. 12/133,432, filed Jun. 5, 2008, which is a divisional of U.S. patent application Ser. No. 10/991,269, filed Nov. 17, 2004 (now U.S. Pat. No. 7,396,673, issued Jul. 8, 2008).

The contents of all of the above are incorporated herein by reference.

BACKGROUND OF THE INVENTION

1. Field of the Invention

The present invention relates to a diaphragm and a device for measuring cellular potential, which is used for measuring an electrophysiological activity of cells, and a manufacturing method of the diaphragm.

2. Background Art

A patch clamp technique is one of conventional methods for elucidating a function of an ion channel existing in a cell membrane or screening (examining) medicines with electrical activities of cells as a reference mark. In the patch clamp technique, a small portion (a patch) of the cell membrane is slightly sucked by a tip portion of a micropipette. Then, by using a fine electrode probe provided in the micropipette, electric current flowing across the patch in the fixed membrane potential is measured. Thus, opening and closing state of one or a few ion channels existing in the patch is electrically measured. This method is one of a few-number of methods capable of investigating a physiological function of a cell on real time basis.

However, the patch clamp technique requires a special technique and skill for preparation and operation of the micropipette, and much time is required to measure one sample. Therefore, this technique is not suitable for an application that requires high-speed screening of a large amount of candidate compounds for a medicine. On the other hand, recently, a flat-shaped fine electrode probe using a fine processing technology has been developed. Such a fine electrode probe is suitable for an automated system that does not require insertion of a micropipette for each individual cell. Hereinafter, the example thereof is described.

For example, Japanese Translation of PCT Publication NO. 2002-518678 discloses a technology for measuring potential-dependent ion channel activities of a test cell attached to an opening of a through-hole by an electrode disposed on the lower side of a plurality of through-holes provided in a cell holding substrate. Furthermore, recently, there has been disclosed a technology for measuring extracellular potential with high degree of accuracy by forming a through-hole of 2.5 µm inside a cell holding substrate made of silicon oxide and allowing this through-hole to hold HEK293 cell which is a kind of human cultured cell line, so as to secure high adhesiveness.

Published PCT International Applications No. 02/055653 pamphlet discloses device 1 for measuring cellular potential shown in FIG. 29. Device 1 for measuring cellular potential includes substrate 2 and well 3 disposed on the upper side of substrate 2. On the upper surface of substrate 2, depression 4 is formed. Through-hole 5 penetrating from the lower part of depression 4 to the lower surface of substrate 2 is provided. In well 3, first electrode 6 is disposed. In through-hole 5, second electrode 7 is disposed. Furthermore, second electrode 7 is connected to a signal detector via wiring 8.

Next, an operating method of device 1 for measuring cellular potential is described. Firstly, test cell (hereinafter, referred to as "cell") 10 and electrolyte 9 are filled in well 3. Cell 10 is captured and held by depression 4. When measurement is carried out, cell 10 is sucked with a suction pump or the like from the lower side of through-hole 5 and held in a state in close contact with an opening of through-hole 5. That is to say, through-hole 5 plays the same role as a tip hole of a glass pipette. The function, pharmacological reaction, or the like of the ion channel of cell 10 can be analyzed by measuring voltage or current between first electrode 6 and second electrode 7 before and after the reaction so as to calculate the potential difference between the inside and outside of cell 10. As mentioned above, by providing depression 4, even when thick substrate 2 is used for securing mechanical strength, the length of through-hole 5 is reduced, and the processing becomes easier. Furthermore, suction force to cell 10 from the lower side of substrate 2 is increased.

However, it has been not possible to control a position of through-hole 5 with high degree of accuracy, conventionally. Consequently, it is not possible to control depth of depression 4 and through-hole 5 with high degree of accuracy. As a result, length of through-hole 5 tends to vary, so that it may be impossible to bring cell 10 into close contact with through-hole 5 appropriately. When cell 10 is sucked, pressure applied to cell 10 becomes short depending upon the length of through-hole 5. As a result, cell 10 may be damaged or the adhesiveness (seal resistance) between cell 10 and through-hole 5 may be reduced. Thus, the measurement accuracy of device 1 for measuring cellular potential may be reduced.

SUMMARY OF THE INVENTION

The present invention relates to a diaphragm in which variations of depths and positions of through-holes are reduced and a method of manufacturing the same. The diaphragm of the present invention is produced as follows. A resist mask having a mask hole is formed on a first surface of a substrate, and a depression is formed on the first surface by isotropic dry etching in a state in which the resist mask is maintained. Then, a through-hole having an opening diameter substantially same as that of the mask hole is formed by allowing the through-hole to penetrate the substrate from the depression to the second surface by anisotropic dry etching while the resist mask is maintained.

Furthermore, the diaphragm of the present invention includes a substrate having a first surface and a second surface opposite the first surface. On the first surface, a depression having a hemispherical shape or a semi-elliptical spherical shape is formed, and a through-hole is formed from the depression to the second surface.

DETAILED DESCRIPTION OF THE EMBODIMENTS

Figure 1:
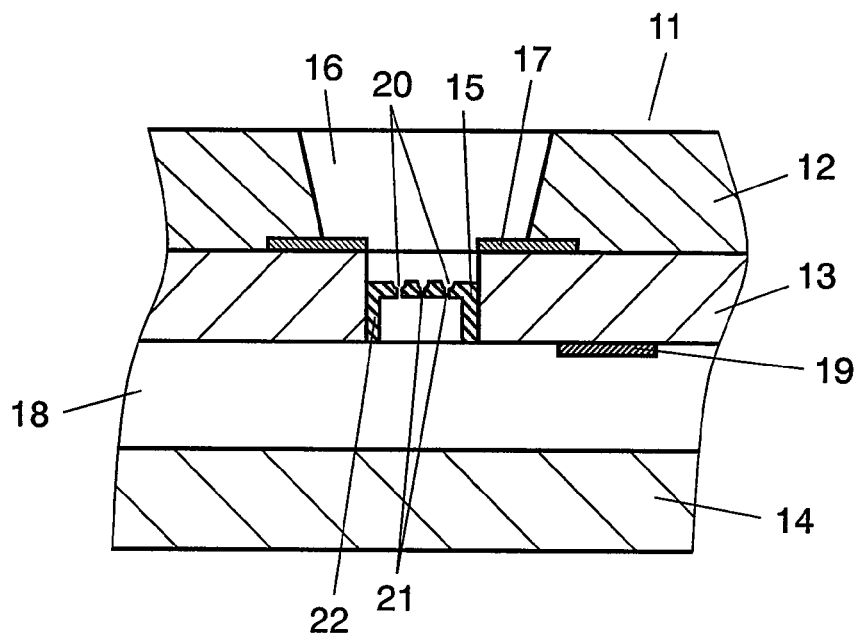
FIG. 1 is a sectional view showing a device for measuring cellular potential in accordance with a first exemplary embodiment of the present invention.

Hereinafter, exemplary embodiments of the present invention are described with reference to drawings. In each exemplary embodiment, the same reference numerals are given to the same configurations as those of the preceding exemplary embodiments, and detailed description therefor may be omitted. Furthermore, the present invention is not limited to each exemplary embodiment. In exemplary embodiments of the invention, the shape of the depression can be similar to a portion of the shape which found in a sphere (e.g. ball shaped) or an oval (e.g. egg shaped). Thus, the depression can have an hemispherical shape meaning that the shape of the depression follows the contour of a portion of a round ball. Alternatively, the depression can have a semi-elliptical shape meaning that the shape of the depression follows the contour of a portion of an oval (e.g. an egg). In an alternative embodiment of the present invention, the shape of the depression can be half the contour of a sphere or half the contour of an oval.

First Exemplary Embodiment

Figure 2:
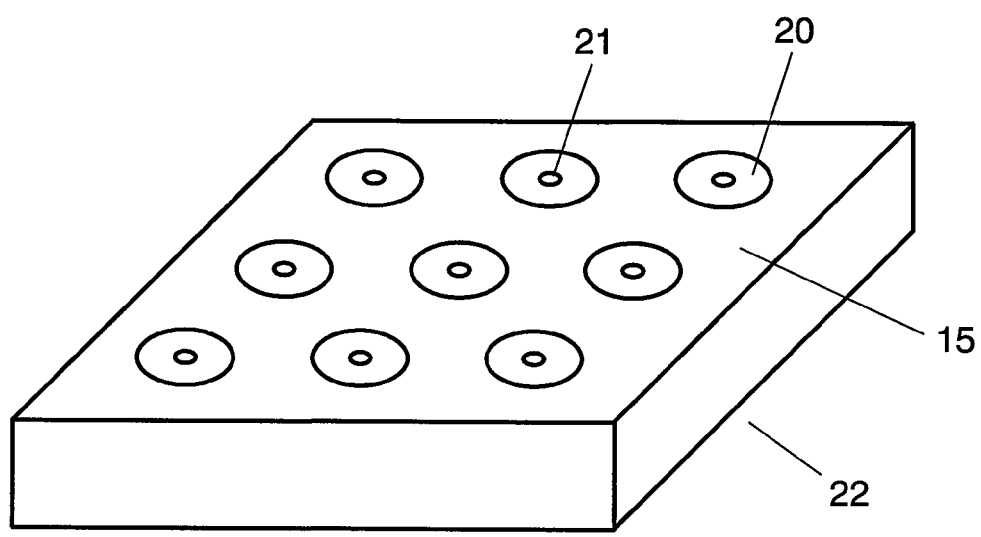
FIG. 2 is a perspective view showing a chip in the device for measuring cellular potential shown in FIG. 1.
Figure 3:
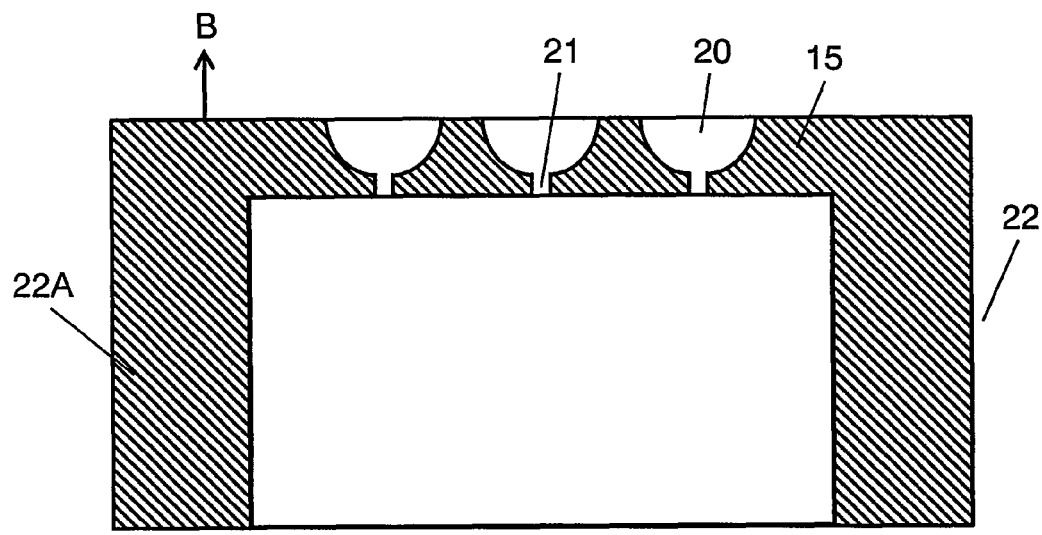
FIG. 3 is a sectional view showing the chip shown in FIG. 2.
Figure 4:
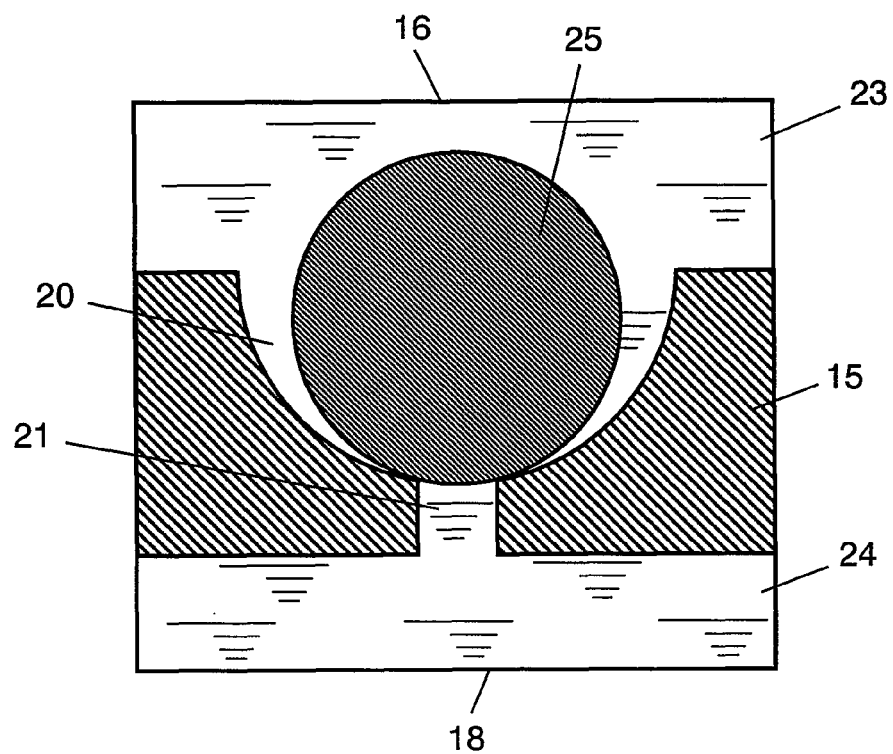
FIG. 4 is an enlarged sectional view showing the chip shown in FIG. 3.

FIG. 1 is a sectional view showing a device for measuring cellular potential in accordance with a first exemplary embodiment of the present invention. FIG. 2 is a perspective view showing a chip in the device for measuring cellular potential shown in FIG. 1. FIG. 3 is a sectional view showing the chip shown in FIG. 2. FIG. 4 is an enlarged sectional view showing the chip shown in FIG. 3. Device 11 for measuring cellular potential includes well plate 12, chip plate 13 disposed on the lower surface of well plate 12, and flow passage plate 14 disposed on the lower surface of chip plate 13.

Into an opening of chip plate 13, chip 22 having substrate 15 forming a diaphragm and side wall 22A standing from the lower surface of substrate 15 is inserted. On the upper side of substrate 15, first electrode tank 16 is provided. Inside first electrode tank 16 and on the upper surface of chip plate 13, first electrode 17 is disposed. Furthermore, on the lower side of chip plate 13 and between chip plate 13 and flow passage plate 14, second electrode tank 18 is provided. Inside second electrode tank 18 and on the lower surface of chip plate 13, second electrode 19 is disposed.

As shown in FIGS. 2 and 3, on an upper surface (first surface) of substrate 15, depression 20 is formed. From the deepest portion of depression 20 to a lower surface (second surface) of substrate 15, through-hole 21 is formed vertically. In other words, substrate 15 includes a first surface and a second surface facing the first surface. On the first surface, depression 20 is formed. From depression 20 to the second surface, through-hole 21 is formed.

Depression 20 is formed in a substantially hemispherical shape that has an inner wall extending from the center of the opening of through-hole 21 to the outer periphery, smoothly curving and standing upwardly. The surface roughness of the inner wall of through-hole 21 is larger than the surface roughness of the inner wall of depression 20.

Substrate 15 is a silicon single crystal plate having a diamond structure with plane orientation of (100). Arrow B in FIG. 3 shows a normal vector of (100) plane orientation. The thickness of substrate 15 is about 20 μm. The (100) plane orientation includes (010) plane orientation and (001) plane orientation, which are equivalent by symmetry of the crystalline structure.

The diameter of the opening of depression 20 is about 30 μm and the minimum opening diameter of through-hole 21 is 3 μm. Since depression 20 has a substantially hemispherical shape, the depth of depression 20 is about 15 μm and the length of through-hole 21 is about 5 μm.

The minimum opening diameter of through-hole 21 and the diameter of the opening of depression 20 are determined depending upon the size, shape, and nature of cell 25 to be tested. When the size of cell 25 is about 5 to 50 μm, for maintaining high adhesiveness between cell 25 and through-hole 21, it is desirable that the minimum opening diameter of through-hole 21 is made to be more than 0 μm and not more than 3 μm. When it is difficult to suck first electrolyte 23, it is preferable that the minimum opening diameter is made to be 0.1 μm or more. It is advantageous because the fluidity is improved. Furthermore, the length of through-hole 21 is set depending upon the pressure at the time of sucking in order to appropriately suck cell 25 into through-hole 21 as mentioned below. In this exemplary embodiment, the length of through-hole 21 is set in the range from about 2 μm to 10 μm.

Next, the operation of device 11 for measuring cellular potential is described. As shown in FIG. 4, firstly, first electrode tank 16 is filled with cell 25 and first electrolyte 23, and second electrode tank 18 is filled with second electrolyte 24.

Then, by depressurizing the lower side of substrate 15 or pressurizing the upper side thereof, cell 25 and first electrolyte 23 are attracted to through-hole 21. At this time, cell 25 is captured by depression 20 and held so as to block the opening of through-hole 21. Thereafter, while cell 25 is held by depression 20 by depressurizing or pressurizing, cells that are not held are removed by washing with physiological saline.

When cell 25 is a mammalian muscle cell, as first electrolyte 23, for example, aqueous solution including 155 mM (mmol/dm$^3$) potassium ion (K$^+$), 12 mM sodium ion (Na$^+$) and 4.2 mM chlorine ion (Cl$^-$) is used. As second electrolyte 24, aqueous solution including 4 mM K$^+$, 145 mM Na$^+$, and 123 mM Cl$^-$ is used. First electrolyte 23 and second electrolyte 24 may have different compositions as in this exemplary embodiment or they may be the same.

Next, by sucking from the lower side of substrate 15 or by infusing medicine such as nystatin from the lower side of substrate 15, a fine hole is formed in cell 25. Thereafter, chemical stimulation or physical stimulation is given to cell 25. The chemical stimulation may include, for example, a chemical medicament or poison. The physical stimulation may include, for example, mechanical displacement, light, heat, electricity, electromagnetic wave, or the like. When cell 25 reacts actively against such stimulation, for example, cell 25 discharges or absorbs various types of ions through an ion channel which the cell membrane possesses. Then, ion current running in cell 25 occurs and the potential gradient inside and outside of cell 25 is changed. This change is detected by measuring a voltage or a current between first electrode 17 and second electrode 19 before and after the reaction.

Next, the invention relating to a method of manufacturing device 11 for measuring cellular potential in accordance with the exemplary embodiments of the present invention is described with reference to FIGS. 5 to 9. FIGS. 5 to 9 are sectional views showing steps of manufacturing the chip shown in FIG. 2, respectively.

Figure 5:
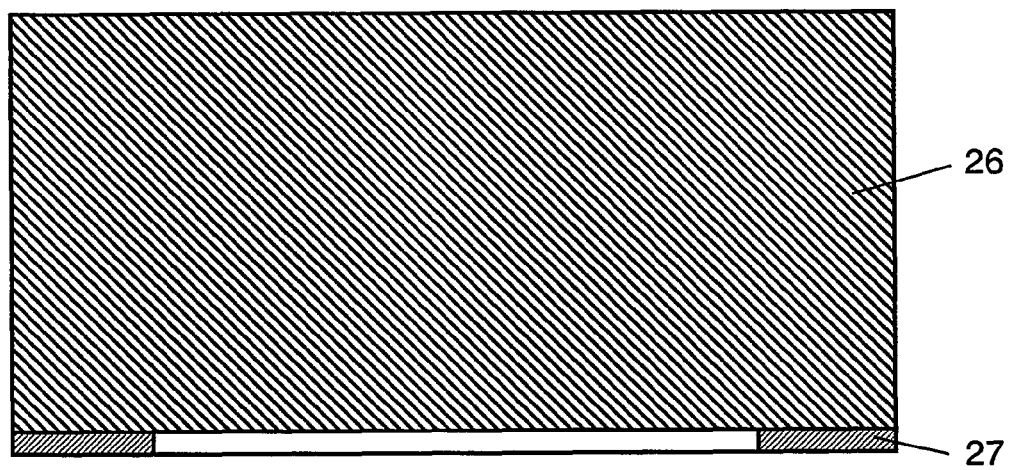
FIG. 5 is a sectional view showing a step of manufacturing the chip shown in FIG. 2.
Figure 6:
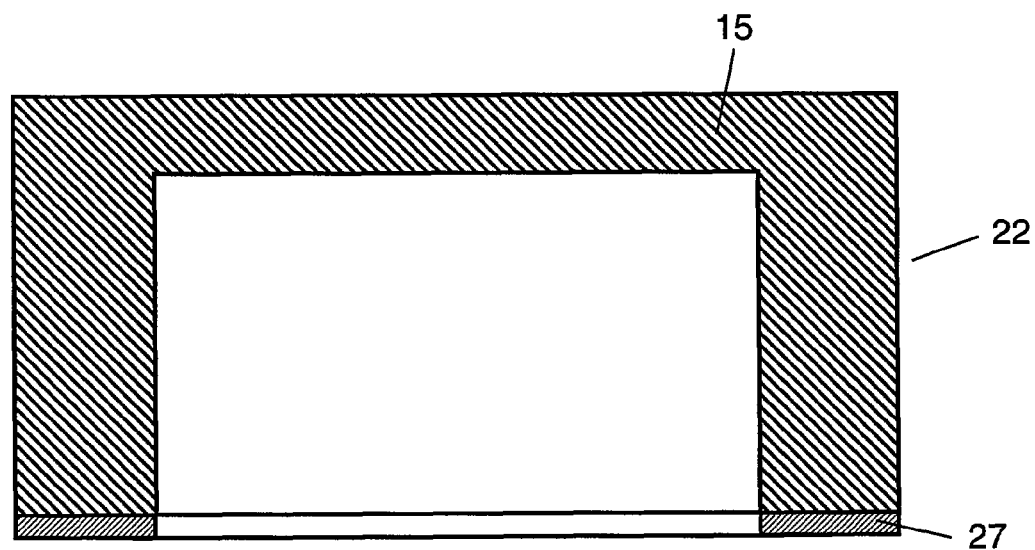
FIG. 6 is a sectional view showing a step of manufacturing the chip shown in FIG. 2, following the step shown in FIG. 5.

Firstly, as shown in FIG. 5, on the lower surface of chip substrate 26 made of a single crystal silicon plate material with (100) plane orientation, resist mask 27 is formed. Next, as shown in FIG. 6, etching is carried out to a predetermined depth from the lower surface of chip substrate 26 as a plate-shaped material. Chip 22 having substrate 15 is formed on the upper surface thereof. Thereafter, resist mask 27 is removed.

Figure 7:
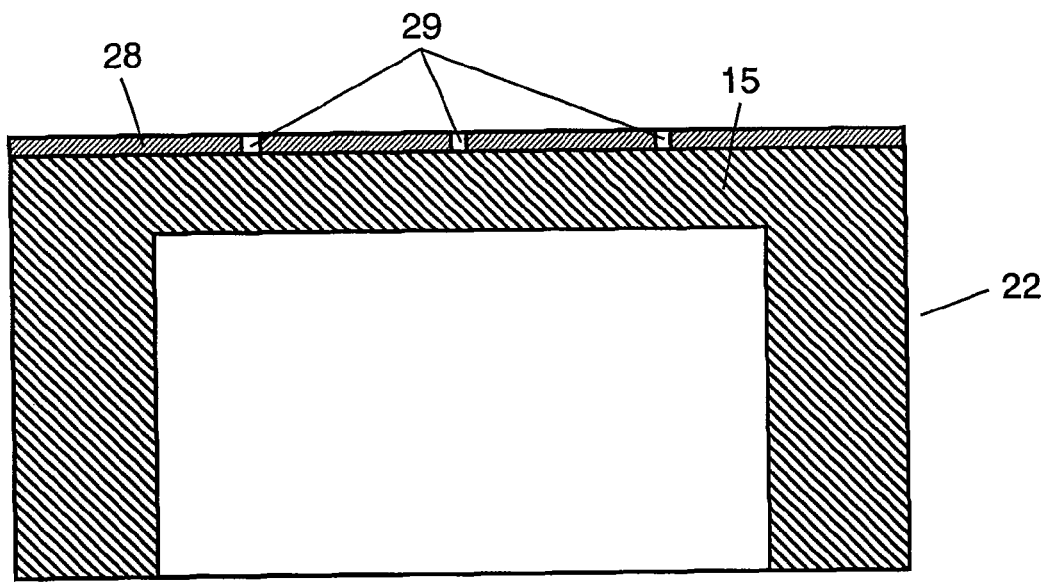
FIG. 7 is a sectional view showing a step of manufacturing the chip shown in FIG. 2, following the step shown in FIG. 6.

Next, as shown in FIG. 7, on the upper surface (first surface) of substrate 15, resist mask 28 is formed. At this time, the shape of mask hole 29 of resist mask 28 is designed so as to be substantially the same as that of the opening of through-hole 21 shown in FIG. 3. In this exemplary embodiment, since the minimum diameter of through-hole 21 is 3 μm, the opening diameter of mask hole 29 is also 3 μm. Furthermore, it is preferable that resist mask 28 is formed of a material that is not easily etched so that the shape of mask hole 29 is not changed. Specifically, it is desirable to use silicon oxide, silicon nitride, silicon oxynitride, or the mixture thereof. By making the thickness of resist mask 28 in a range from 1 μm to 3 μm, the state of base substrate 15 can be seen.

Figure 8:
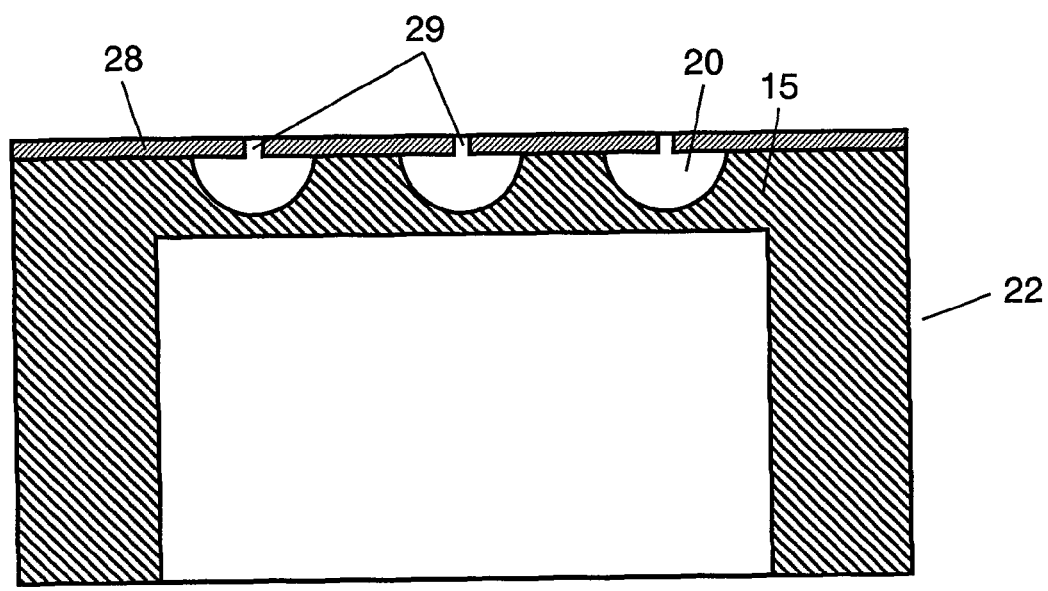
FIG. 8 is a sectional view showing a step of manufacturing the chip shown in FIG. 2, following the step shown in FIG. 7.

Thereafter, as shown in FIG. 8, depression 20 is formed on the upper surface of substrate 15 by dry etching. When substrate 15 is silicon, as an etching gas for promoting etching, SF$_6$, CF$_4$, NF$_3$, or XeF$_2$ or the mixed gas of two or more of them can be used. Since these have an effect of promoting etching not only in the depth direction of silicon but also in the horizontal direction of silicon, substrate 15 is etched in a shape of a hemispherical bowl. Thus, in this step, isotropic dry etching is carried out on substrate 15, and thereby depression 20 having a substantially hemispherical shape is formed.

Figure 9:
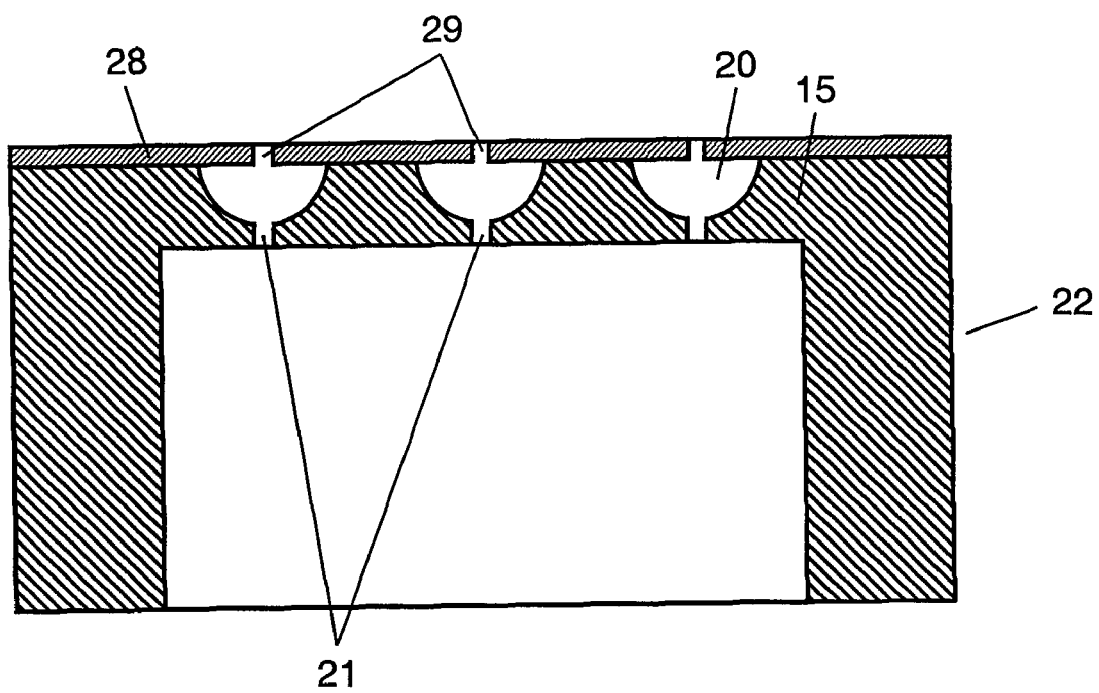
FIG. 9 is a sectional view showing a step of manufacturing the chip shown in FIG. 2, following the step shown in FIG. 8.

Next, as shown in FIG. 9, in a state in which resist mask 28 is disposed, through-hole 21 penetrating in the vertical direction from the deepest portion of depression 20 to the lower surface (second surface) of substrate 15 is formed. When through-hole 21 is formed, dry etching processing is carried out by using the above-mentioned etching gas (at least one of SF$_6$, CF$_4$, NF$_3$, and XeF$_2$) for promoting etching and a gas for suppressing the etching alternately. As the gas for suppressing etching, CHF$_3$, C$_4$F$_8$, or a mixed gas thereof can be used. When such a gas is blown to the etched wall surface, a protective film that is polymer of CF$_2$ is formed. Therefore, through-hole 21 can be allowed to proceed from the deepest portion of depression 20 to the lower surface of substrate 15. Thus, in this step, anisotropic dry etching is carried out on substrate 15, and thereby through-hole 21 is formed.

Figure 10A:
FIG. 10A is a view showing a scanning electron microscope image of the device for measuring cellular potential shown in FIG. 1.
Figure 10B:
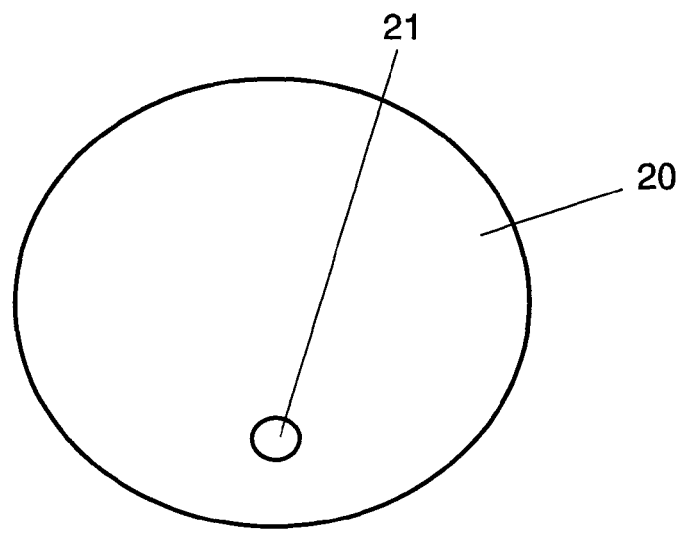
FIG. 10B is a schematic view showing the scanning electron microscope image shown in FIG. 10A.

As mentioned above, when resist mask 28 is removed after through-hole 21 is formed, substrate 15 provided with depression 20 and through-hole 21 is completed as shown in the scanning electron microscope image of FIG. 10A and the schematic view of FIG. 10B. Note here that FIG. 10A shows an observation result shown from the angle of 30° with respect to the surface of substrate 15.

Note here that by carrying out an etching process as mentioned above in a state in which substrate 15 is inclined obliquely, through-hole 21 may be formed on the lower surface of substrate 15 not only perpendicularly but also obliquely.

As mentioned above, after through-hole 21 is formed, as shown in FIG. 1, first electrode 17 is formed on the upper surface of chip plate 13 and second electrode 19 is patterned on the lower surface thereof by metal deposition, electroless plating, or the like. First electrode 17 and second electrode 19 may be formed for each chip 22 or may be shared by a plurality of chips 22.

Next, well plate 12 is attached to the upper surface of chip plate 13 by using an adhesive agent, and chip 22 is mounted on the opening of chip plate 13. Then, flow passage plate 14 is attached to the lower surface of chip plate 13. Thus, first electrode tank 16 is disposed on the upper side of substrate 15, and second electrode tank 18 is disposed on the lower side of substrate 15, respectively. Device 11 for measuring cellular potential is completed.

In this exemplary embodiment, as shown in FIG. 10A, a silicon single crystal plate having a diamond structure with (100) plane orientation is used as substrate 15. Therefore, even if depression 20 is formed by dry etching, concavity and convexity on the surface of depression 20 are reduced, so that etching proceeds uniformly. As a result, formed depression 20 has a shape that is excellent in symmetry with respect to opening of through-hole 21 as the center. Thus, the depth of depression 20 can be easily calculated from the opening diameter of depression 20 that can be measured from the outer appearance. Then, from the depth of depression 20 and thickness of substrate 15, the length of through-hole 21 can be calculated. As a result, variation in the length of through-hole 21 is reduced, so that the measurement accuracy of device 11 for measuring cellular potential can be improved.

Furthermore, as mentioned above, the surface roughness of the inner wall of depression 20 is reduced. Therefore, by capturing cell 25 by smooth depression 20, the adhesiveness (seal resistance) between through-hole 21 and cell 25 can be enhanced. As a result, the measurement accuracy of device 11 for measuring cellular potential can be improved.

Figure 11:
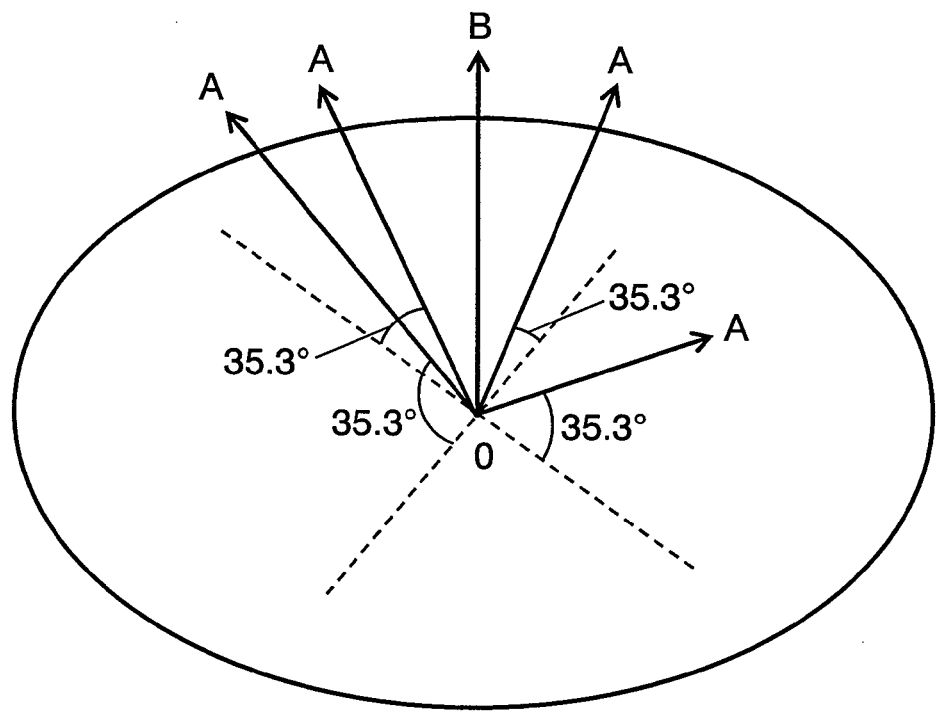
FIG. 11 is a schematic view showing a position of (111) plane orientation in a single crystal silicon plate of (100) plane orientation, which is a substrate of the device for measuring cellular potential, in accordance with the first exemplary embodiment of the present invention.

Herein, the reason why the surface roughness of the inner wall of depression 20 can be reduced is described with reference to FIG. 11. FIG. 11 is a schematic view showing substrate 15 made of a single crystal silicon plate with (100) plane orientation used in this exemplary embodiment. Vector A shows a normal vector of (111) plane orientation of substrate 15 with (100) plane orientation. Vector B is a normal vector of (100) plane orientation.

Vector A declines at 35.3° with respect to the upper surface of substrate 15 and has (111) plane orientation at 54.7° with respect to the upper surface of substrate 15. Substrate 15 has such vectors A at equal positions in a concentric hemispherical shape with respect to center O.

Silicon forming substrate 15 has a diamond crystalline structure in which all silicon atoms are bonded to each other with four binding members. Then, in this (111) plane orientation, the density of silicon atoms is maximum. Three of the binding members of silicon extend from the surface of substrate 15 to the lower part, and only one binding member is free and present on the surface layer. On the other hand, in (100) plane orientation, two free binding members are present in a way in which they protrude from the surface of substrate 15 and show a high reactivity. Therefore, the etching in the direction of normal vector B of (100) plane orientation is much faster than that of the etching in the direction of normal vector A of (111) plane orientation.

That it so say, in silicon substrate 15 with (100) plane orientation used in this exemplary embodiment, since the etching in the direction of vector B is fast, the etching in the depth direction of depression 20 is promoted. Furthermore, since vectors A are present equally in the radial direction, the etching easily proceeds symmetrically. Thus, it is thought that the surface roughness of the inner wall of depression 20 can be reduced. As a result, the shape of depression 20 has a hemispherical shape that is excellent in symmetry.

The etching conditions such as etching processing time and the like can be easily adjusted while confirming the appearance of depression 20 by using an optical microscope or the like. Thus, the manufacturing process can be facilitated. Then, it is possible to set the length of through-hole 21 with high degree of accuracy from the depth of depression 20 and the thickness of substrate 15. Furthermore, since the surface of depression 20 becomes smooth, the adhesiveness between cell 25 and through-hole 21 is enhanced and the measurement accuracy of device 11 for measuring cellular potential is improved.

As the etching gas used for dry etching, $N_2$, Ar, He, $H_2$ or a carrier gas that is a mixed gas thereof may be used. Furthermore, the molar ratio of the etching gas to the carrier gas is desired to be more than 0 and not more than 2.0. By using a carrier gas having such composition and molar ratio, the above-mentioned etching gas is diffused uniformly and the smoothness of depression 20 can be improved. Furthermore, complicated factors affecting the shape such as concavity and convexity is extremely reduced so as to smooth the depression, thereby easily allowing a plurality of depressions 20 to be formed in substantially the same shape.

In a dry etching processing, an etching gas is infused into the inside of depression 20 from the upper side of resist mask 28, and filled therein for a predetermined time. Thereafter, the etching gas is sucked (removed) and recovered, and the etching gas is filled and recovered again. It is preferable that such an operation is repeated a plurality of times. Thus, an etching gas can be diffused uniformly. Then, slight concavity and convexity are provided on the inner wall of through-hole 21 repeatedly so as to form through-hole 21 substantially linearly. Therefore, the length of through-hole 21 can be designed with high degree of accuracy. At the same time, in the vicinity of opening through-hole 21, cell 25 enters the concavity and convexity, so that the adhesiveness between cell 25 and through-hole 21 is improved.

Furthermore, in this exemplary embodiment, depression 20 and through-hole 21 are formed sequentially by dry etching using one resist mask 28 as shown in FIG. 9. Therefore, the position of the opening of through-hole 21 can be determined accurately in the deepest portion of depression 20. Since cell 25 drops by gravity, it is easily trapped in the deepest portion of depression 20. Therefore, by setting the position of the opening of through-hole 21 to be the deepest portion of depression 20, the measurement accuracy of device 11 for measuring cellular potential can be improved. Furthermore, a plurality of pairs of depression 20 and through-hole 21 can be formed in substantially the same shape. Since variation in the sucking force applied to cell 25 and variation of the measurement error due to variation of shapes between the pairs are reduced, the measurement accuracy is improved.

Furthermore, as compared with the case where two kinds of the resist masks are used, manufacturing time can be omitted, thus contributing to the reduction of the cost.

In this exemplary embodiment, depression 20 has an inner wall having a hemispherical shape and smoothly curving and standing from the opening of through-hole 21 to the upper side of the outer periphery. Cell 25 can fall down along this inner wall smoothly toward through-hole 21 by gravity. Therefore, cell 25 can be captured by depression 20 appropriately. The adhesiveness between cell 25 and through-hole 21 is enhanced, thus contributing the improvement of the measurement accuracy of device 11 for measuring cellular potential.

Second Exemplary Embodiment

Figure 12:
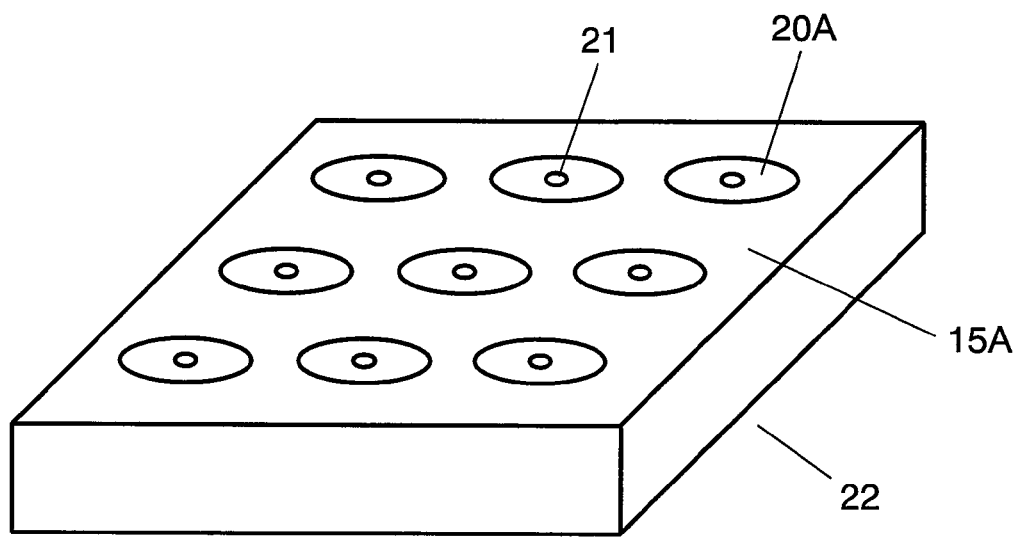
FIG. 12 is a perspective view showing a chip in a device for measuring cellular potential in accordance with a second exemplary embodiment of the present invention.
Figure 13:
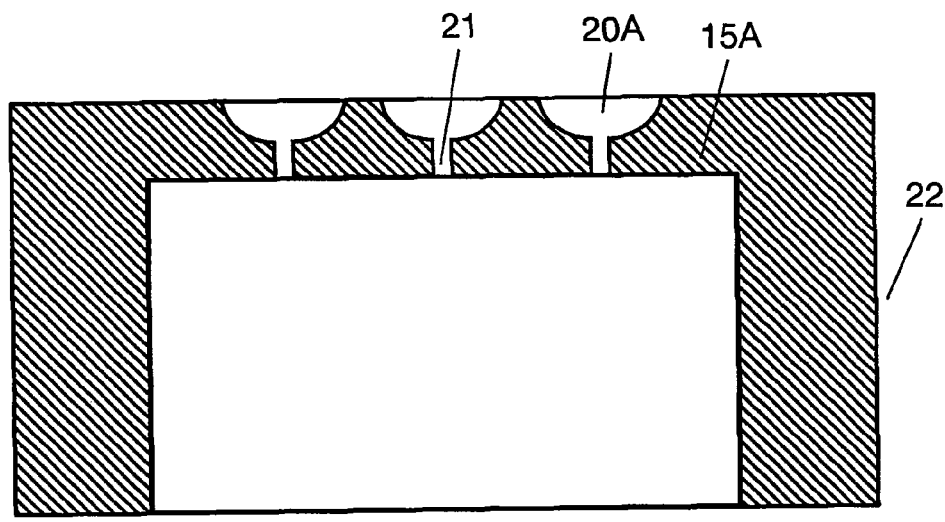
FIG. 13 is a sectional view showing the chip shown in FIG. 12.
Figure 14:
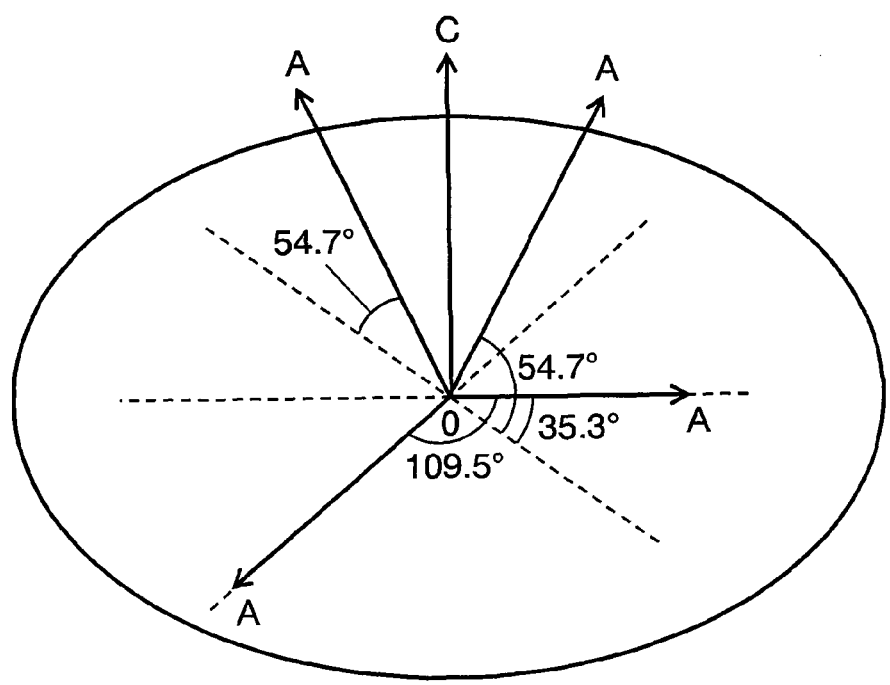
FIG. 14 is a schematic view showing a position of (111) plane orientation in a single crystal silicon plate of (110) plane orientation, which is a substrate of the device for measuring cellular potential, in accordance with the second exemplary embodiment of the present invention.

FIG. 12 and FIG. 13 are a perspective view and a sectional view showing a chip in a device for measuring cellular potential in accordance with a second exemplary embodiment of the present invention, respectively. FIG. 14 is a schematic view showing the positions of the (111) plane orientation in a single crystal silicon plate with (110) plane orientation, which is a substrate of the device for measuring cellular potential in accordance with this exemplary embodiment. This exemplary embodiment is the same as the first exemplary embodiment except that a single crystal silicon with (110) plane orientation is used as a material for substrate 15A in this exemplary embodiment. The (110) plane orientation includes (011) plane orientation and (101) plane orientation which are equivalent by symmetry of the crystalline structure.

As shown in FIG. 14, substrate 15A of a single crystal silicon plate with (110) plane orientation has (111) plane orientation at 90° and 35.3° with respect to the surface. That is to say, vector A is a normal vector of (111) plane orientation in (110) plane orientation and declines at 90° or 54.7° from the center O of substrate 15A. Furthermore, vector C is a normal vector of (110) plane orientation and the dotted lines show reference lines on substrate 15A.

In this exemplary embodiment, unlike the first exemplary embodiment, the shape of depression 20A is substantially semi-elliptical sphere. This is because normal vectors A of (111) plane orientation are not disposed equally in a concentric hemispherical shape from center O as shown in FIG. 14, the etching shape on the surface of substrate 15A becomes a substantially elliptical shape.

Thus, in this exemplary embodiment, as substrate 15A, a single crystal silicon plate with (110) plane orientation is used. Also in this case, the surface roughness of the inner wall of depression 20A is reduced and depression 20A has a smooth shape. Therefore, depression 20A has a shape that is excellent in symmetry with respect to the opening of through-hole 21 as a center. Therefore, if the relation between the opening diameter and depth of depression 20A is calculated for each etching condition, the depth of depression 20A can be calculated from the opening diameter of depression 20A that can be calculated from the appearance, when the etching condition is the same. As a result, the length of through-hole 21 can be designed with high degree of accuracy.

In this exemplary embodiment, unlike the first exemplary embodiment, only one free binding member of silicon atom exists on the surface of the (110) substrate, however, two binding members are present in parallel on the surface of substrate 15A. Therefore, the binding members are in the state in which they are easily reacted with each other. Therefore, when silicon substrate 15A with (110) plane orientation is used, similar to the case where silicon substrate 15 with (100) plane orientation is used, the etching in the direction of normal vector C of (110) plane orientation becomes faster. Then, it is possible to suppress the remarkable increase in the etching speed of silicon atoms in the horizontal direction. Furthermore, normal vectors A are disposed not in a hemispherical shape, but in a radial shape with symmetry. Therefore, it is estimated that the etching proceeds left-right symmetrically with respect to normal vector C. Although not shown, also in this exemplary embodiment, by using one resist mask, depression 20A is formed by isotropic dry etching and then through-hole 21 is formed by anisotropic dry etching.

As mentioned above, also in this exemplary embodiment, the surface roughness of the inner wall of depression 20A is reduced and depression 20A has a smooth shape. Therefore, the adhesiveness between through-hole 21 and cell 25 is enhanced and the measurement accuracy of device 11 for measuring cellular potential is improved.

Furthermore, in this exemplary embodiment, the shape of depression 20A becomes substantially semi-elliptical sphere. Therefore, when cell 25 having an elliptical spherical shape is intended to be measured, cell 25 can be stably held in depression 20A, thus contributing to the improvement of the measurement accuracy.

Third Exemplary Embodiment

Figure 15:
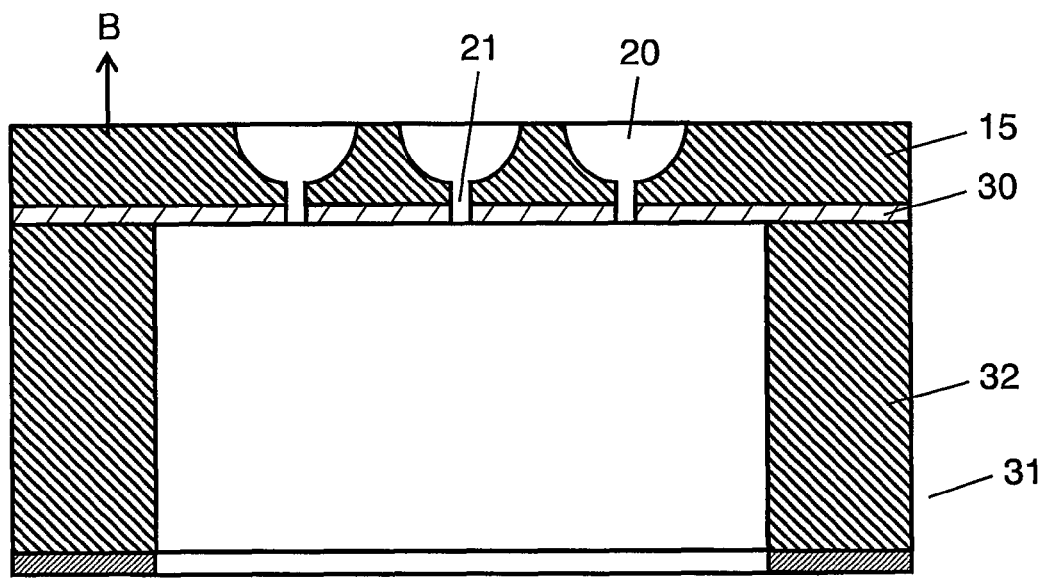
FIG. 15 is a sectional view showing a chip in a device for measuring cellular potential in accordance with a third exemplary embodiment of the present invention.

FIG. 15 is a sectional view showing a chip in a device for measuring cellular potential in accordance with a third exemplary embodiment of the present invention. The third exemplary embodiment is different from the first exemplary embodiment in that silicon oxide layer 30 is formed on a lower surface (second surface) of substrate 15. In other words, chip 31 of this exemplary embodiment has substrate 15 having a thickness of about 20 µm, silicon oxide layer 30 having a thickness of about 2 µm, and lower silicon layer 32 having a thickness of about 400 to 500 µm. Silicon oxide layer 30 is disposed on the lower surface of substrate 15. Lower silicon layer 32 is formed on the lower surface of silicon oxide layer 30 on a periphery of substrate 15, and forms a side wall standing from the lower surface of substrate 15. Lower silicon layer 32 functions as a frame body for holding substrate 15. When lower silicon layer 32 is thick even if the substrate 15 is thin, the strength of chip 31 can be increased. Note here that lower silicon layer 32 is thicker than the substrate 15 in this exemplary embodiment. Substrate 15 is made of a single crystal silicon plate with (100) plane orientation. The other configurations are the same as those in the first exemplary embodiment. Note here that vector B shown in FIG. 15 shows a normal vector of (100) plane orientation.

Next, a method of manufacturing chip 31 is described with reference to FIGS. 16 to 21. FIGS. 16 to 21 are sectional views showing steps of manufacturing the chip shown in FIG. 15.

Figure 16:
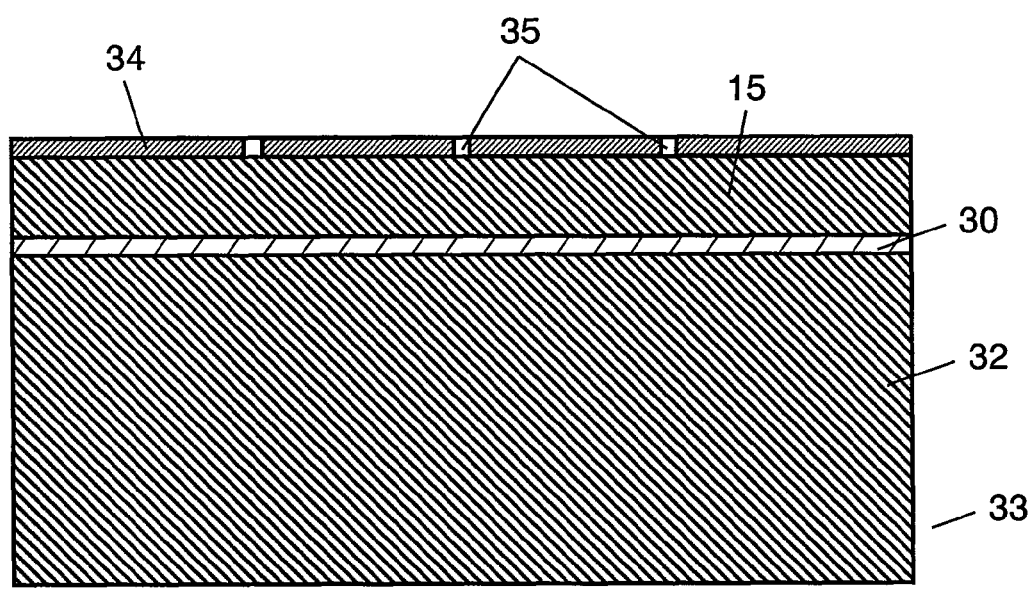
FIG. 16 is a sectional view showing a step of manufacturing the chip shown in FIG. 15.

Firstly, as shown in FIG. 16, on the upper surface of substrate 15 of chip substrate 33 as a plate-shaped material, resist mask 34 is formed. Chip substrate 33 is formed of three layers, i.e., substrate 15, silicon oxide layer 30 and lower silicon layer 32. Substrate 15 is made of a single crystal silicon plate having a thickness of about 20 µm and having (100) plane orientation. Silicon oxide layer 30 having a thickness of about 2 µm is disposed on the lower surface of substrate 15. Lower silicon layer 32 having a thickness of about 400 to 500 µm is disposed on the lower surface of silicon oxide layer 30.

Mask hole 35 of resist mask 34 is designed so that the shape of mask hole 35 is substantially the same shape of through-hole 21 of FIG. 15. In this exemplary embodiment, since the minimum opening diameter of through-hole 21 is 3 μm, the opening diameter of mask hole 35 is also 3 μm.

Figure 17:
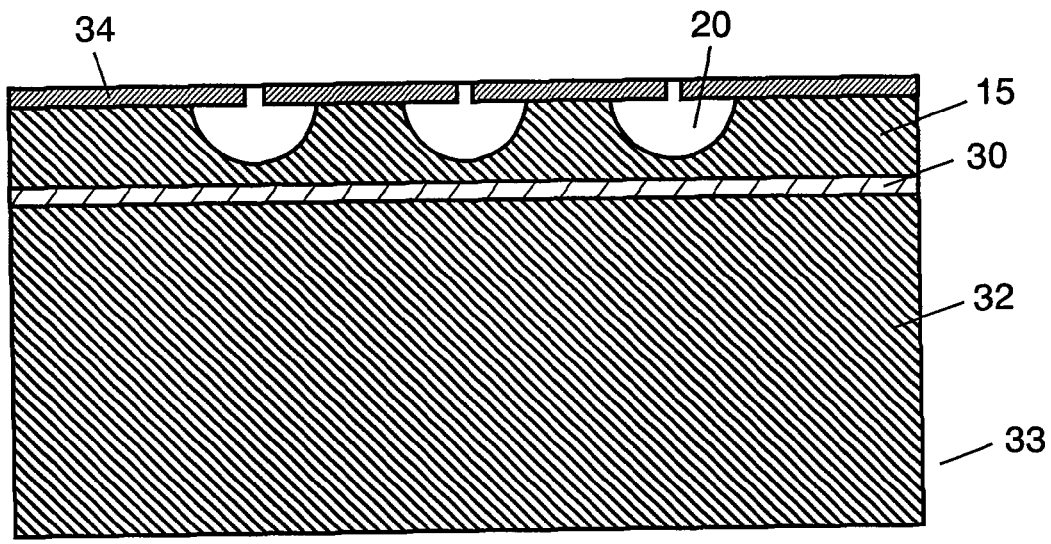
FIG. 17 is a sectional view showing a step of manufacturing the chip shown in FIG. 15, following the step shown in FIG. 16.

Thereafter, as shown in FIG. 17, dry etching is carried out from the upper surface of substrate 15 by using an etching gas selected from at least any one of $SF_6$, $CF_4$, $NF_3$, and $XeF_2$, and thus depression 20 is formed. The method of forming depression 20 is the same as that shown in the first exemplary embodiment.

Figure 18:
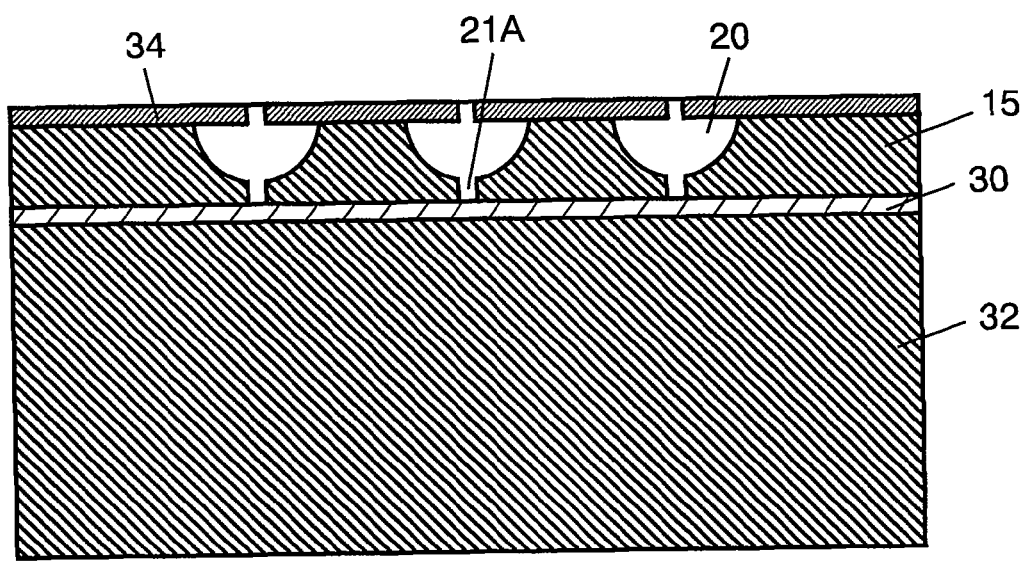
FIG. 18 is a sectional view showing a step of manufacturing the chip shown in FIG. 15, following the step shown in FIG. 17.

Next, as shown in FIG. 18, dry etching is carried out from depression 20 to the lower surface of substrate 15 so as to form hole 21A that is to be through-hole 21. At this time, when $SF_6$ for promoting etching of silicon is used as the dry etching gas, by the difference in the etching rate, silicon oxide layer 30 becomes an etching stop layer. That is to say, silicon oxide layer 30 is an etching stop layer having a smaller etching rate than that of a material constituting substrate 15. Then, it is possible to form the length of hole 21A constantly as designed. Thus, hole 21A can be formed by a simple method with high degree of accuracy. Thus, when substrate 15 is produced by etching chip substrate 33 having silicon oxide layer 30 as an etching stop layer inside thereof, the thickness of substrate 15 can be controlled.

Figure 19:
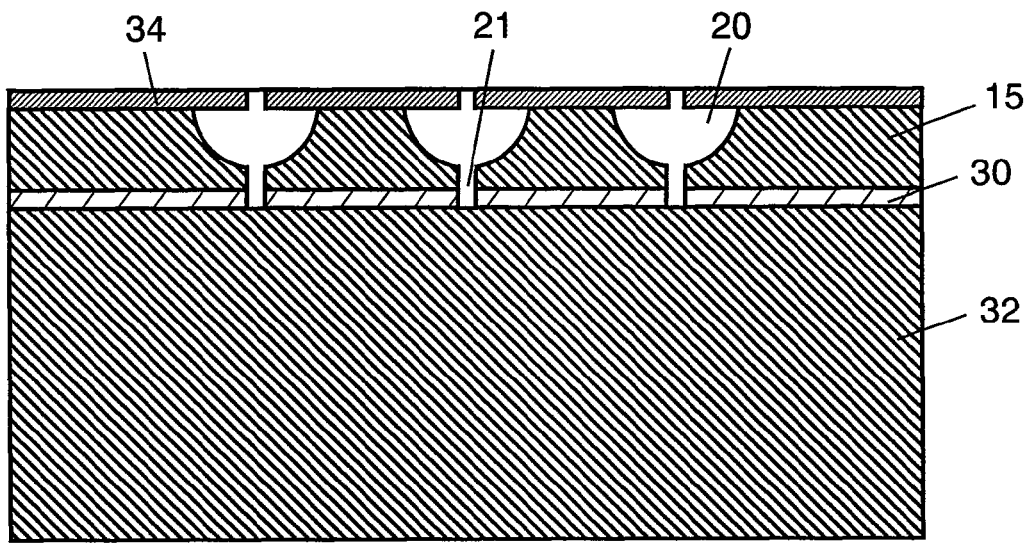
FIG. 19 is a sectional view showing a step of manufacturing the chip shown in FIG. 15, following the step shown in FIG. 18.
Figure 20:
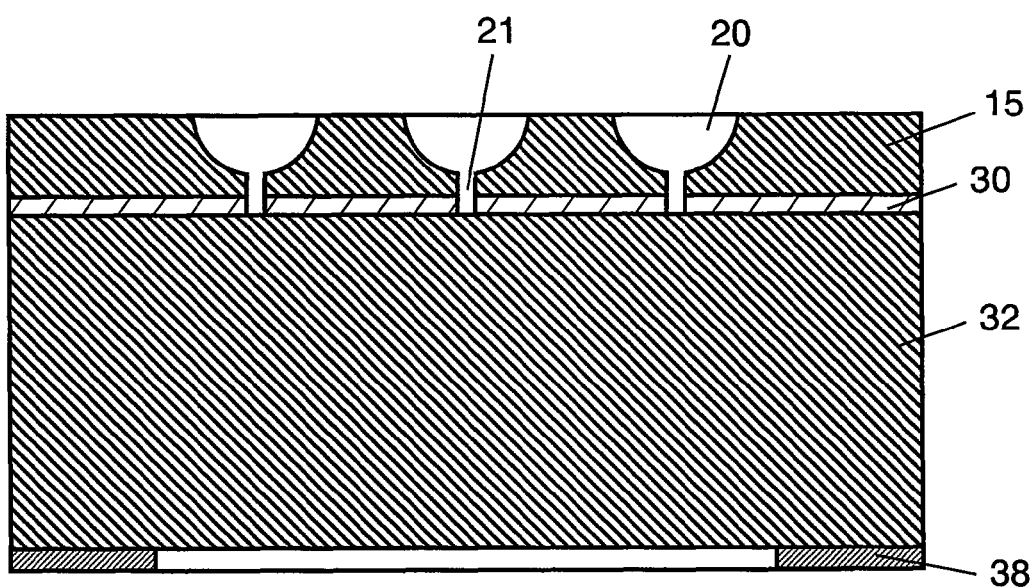
FIG. 20 is a sectional view showing a step of manufacturing the chip shown in FIG. 15, following the step shown in FIG. 19.
Figure 21:
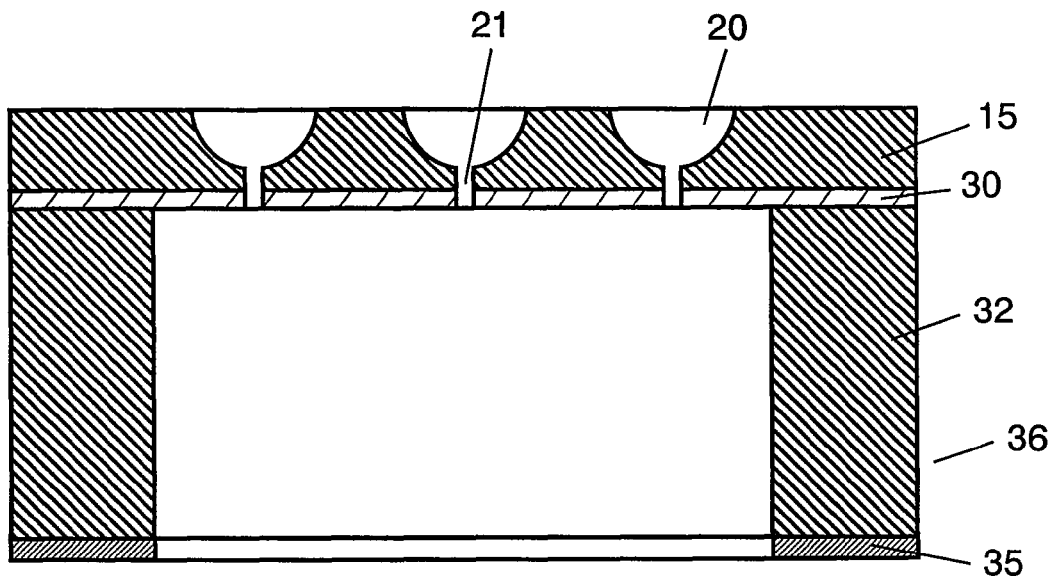
FIG. 21 is a sectional view showing a step of manufacturing the chip shown in FIG. 15, following the step shown in FIG. 20.

Next, as shown in FIG. 19, silicon oxide layer 30 is etched from the upper surface of substrate 15 by using a gas such as $CF_4$. Thus, through-hole 21 is formed. Thereafter, resist mask 34 is removed. Then, as shown in FIG. 20, on the lower surface of lower silicon layer 32, resist mask 38 is formed. Thereafter, as shown in FIG. 21, etching is carried out from the lower surface of lower silicon layer 32 to silicon oxide layer 30 so as to complete through-hole 21. At this time, since silicon oxide layer 30 works as an etching stop layer, the thickness of substrate 15 can be adjusted with high degree of accuracy. As a result, the length of through-hole 21 can be made with high degree of accuracy. The other effects are the same as those in the first exemplary embodiment, so that the description thereof is omitted herein.

Note here that for substrate 15, a single crystal silicon layer with (100) plane orientation is used. However, even if a single crystal silicon layer with (110) plane orientation is used, the surface roughness of depression 20 can be reduced and the surface shape can be smoothed. Furthermore, the shape of the inner wall can be made to be a shape that is free from the level difference and excellent in symmetry. Furthermore, when the surface has less concavity and convexity, the factors affecting the shape are reduced. Therefore, when a plurality of depressions 20 is formed, the uniformity of the shapes thereof can be enhanced. That is to say, the same effect of the second exemplary embodiment can be obtained.

Furthermore, in this exemplary embodiment, when substrate 15 is made of silicon, silicon oxide layer 30 is used as the etching stop layer. However, besides, the etching stop layer may be formed of silicon nitride ($Si_3N_4$).

Fourth Exemplary Embodiment

Figure 22:
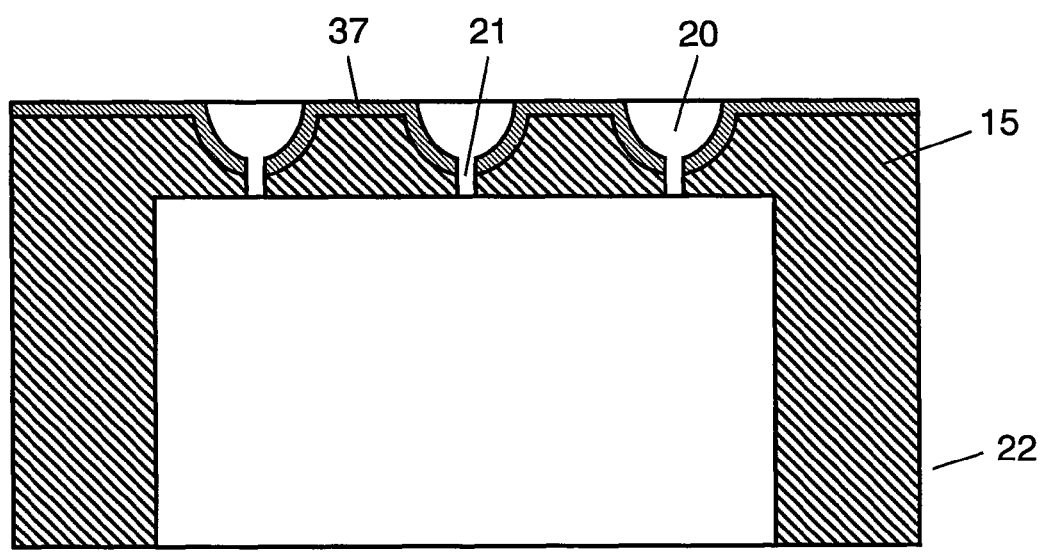
FIG. 22 is a sectional view showing a chip in a device for measuring cellular potential in accordance with a fourth exemplary embodiment of the present invention.

FIG. 22 is a sectional view showing a chip in a device for measuring cellular potential in accordance with a fourth exemplary embodiment of the present invention. This exemplary embodiment is different from the first exemplary embodiment in that the upper surface of substrate 15 and the inner wall of depression 20 are covered with silicon oxide film 37. That is to say, at least the surface of depression 20 is provided with film 37 of an insulating material. The other configurations are the same as those of the first exemplary embodiment.

Thus, the surface roughness of the inner wall of depression 20 is reduced and the mer wall is smoothed. Therefore, cell 25 is easily brought into close contact with the opening of through-hole 21 and the measurement accuracy of device 11 for measuring cellular potential is improved. Furthermore, by using an insulating material as a material of film 37, the insulating property of the upper part and lower part of through-hole 21 is enhanced, thus contributing to the improvement of reliability of the measurement accuracy.

As materials of film 37, silicon nitride, silicon oxynitride, or the mixture thereof can be used besides silicon oxide. For example, film 37 made of silicon oxide or silicon nitride can be formed by sputtering silicon oxide or silicon nitride. With such a method, film 37 is not easily formed on the inner wall of through-hole 21 having a large aspect ratio. Film 37 is formed only on the upper surface of substrate 15 and on the inner wall of depression 20. Furthermore, when chip 22 made of silicon is thermally treated under oxygen atmosphere, silicon oxide film 37 is formed on the entire surface of chip 22. Thus, as film 37, film 37 made of an insulating material may be provided on at least the surface of depression 20.

When silicon oxide is used as film 37, as compared with the case where film 37 is not used for covering, the hydrophilic property of the inner wall of depression 20 is improved. In general, since the surface of cell 25 has a hydrophilic property, when the hydrophilic property of the inner wall of depression 20 is improved, cell 25 is brought into close contact with and held by the inner wall of depression 20. Specifically, when film 37 is provided, as compared with the case where film 37 is not provided, the contact angle of cell 25 and the surface of depression 20 is reduced to about ⅓. The other effects are the same as those of the first exemplary embodiment, so that the description is omitted.

Fifth Exemplary Embodiment

Figure 23:
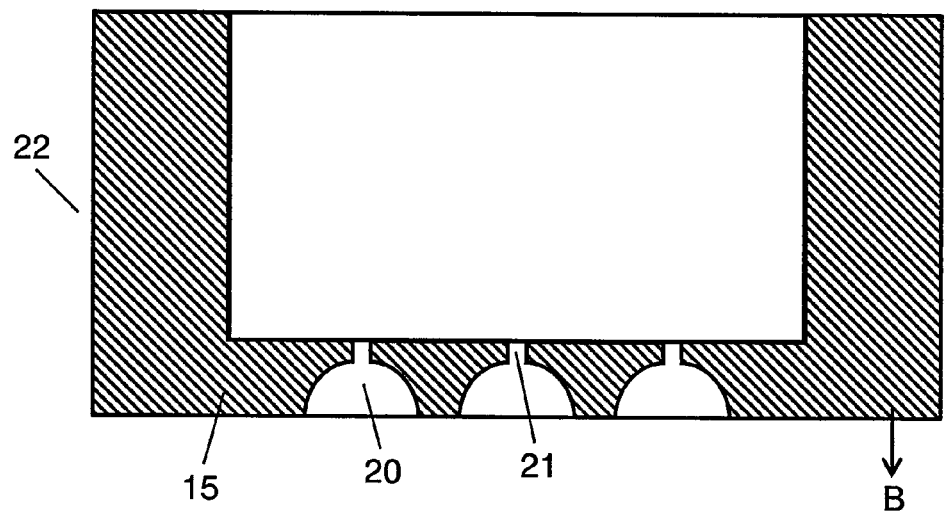
FIG. 23 is a sectional view showing a chip in a device for measuring cellular potential in accordance with a fifth exemplary embodiment of the present invention.
Figure 24:
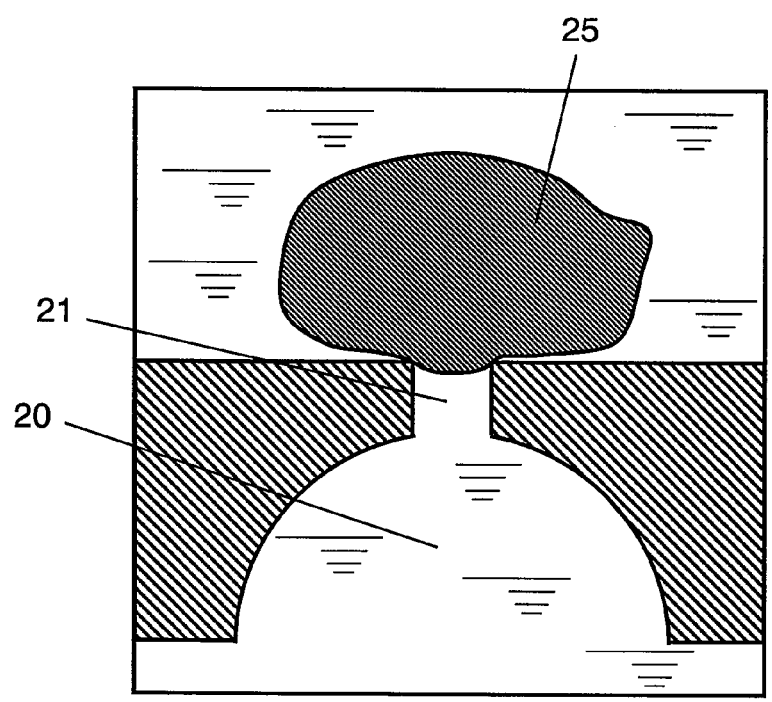
FIG. 24 is an enlarged sectional view showing the chip shown in FIG. 23.

FIG. 23 is a sectional view showing a chip in a device for measuring cellular potential in accordance with a fifth exemplary embodiment of the present invention. FIG. 24 is an enlarged sectional view of the chip shown in FIG. 23. This exemplary embodiment is different from the first exemplary embodiment in that chip 22 is inverted upside down and disposed on chip plate 13 shown in FIG. 1.

That is to say, in this exemplary embodiment, substrate 15 is a silicone plate with (100) plane orientation. On the upper surface (second surface) of substrate 15, through-hole 21 is formed, and on the lower surface (first surface), depression 20 is formed. Depression 20 has an inner wall having a substantially hemispherical shape, extending from the opening of through-hole 21 to the outer periphery, smoothly curving and connected to the upper surface.

Thus, in this exemplary embodiment, the variation of the length of through-hole 21 is reduced. Moreover, the change of the sectional area of the flow passage from through-hole 21 to second electrode tank 18 shown in FIG. 1 becomes gentle. The flow resistance is reduced, and electrolyte or the like easily flows. Furthermore, sucking from the lower part of substrate 15 is easily carried out. Therefore, cell 25 can be brought into close contact with the opening of the through-hole 21. Furthermore, liquid medicine such as nystatin that is infused from the lower part of substrate 15 can easily flow into through-hole 21 and can rapidly reach cell 25.

Furthermore, since the inner wall surface of depression 20 is smooth, bubbles generated on the inner wall of depression 20 are reduced. Therefore, it is possible to suppress the difficulty, due to the presence of bubbles, in transmitting the pressure when cell 25 is sucked into through-hole 21. Therefore, cell 25 can be appropriately brought into close contact with through-hole 21.

Still further, it is preferable that the surface roughness of through-hole 21 is made to be larger than the surface roughness of depression 20. Thus, the concavity and convexity on the inner wall of through-hole 21 work as an anchor with respect to cell 25. Even when depression 20 is not formed on the upper surface of substrate 15, the adhesiveness with respect to through-hole 21 can be further improved and the measurement accuracy can be enhanced. Besides, the description of the same configuration and effects as those in the first exemplary embodiment is omitted.

Note here that in this exemplary embodiment, as substrate 15, a silicon plate with (100) plane orientation is used. However, when a silicon plate with (110) plane orientation is used as substrate 15 similar to the second exemplary embodiment, the same effect can be obtained. Furthermore, the inner wall of depression 20 or the lower surface of substrate 15 may be covered with insulating film 37 made of silicon oxide and the like, similar to the fourth exemplary embodiment. Thus, the inner wall of depression 20 is further smoothed and electric insulating property of the upper part and lower part of through-hole 21 is enhanced.

Sixth Exemplary Embodiment

Figure 25:
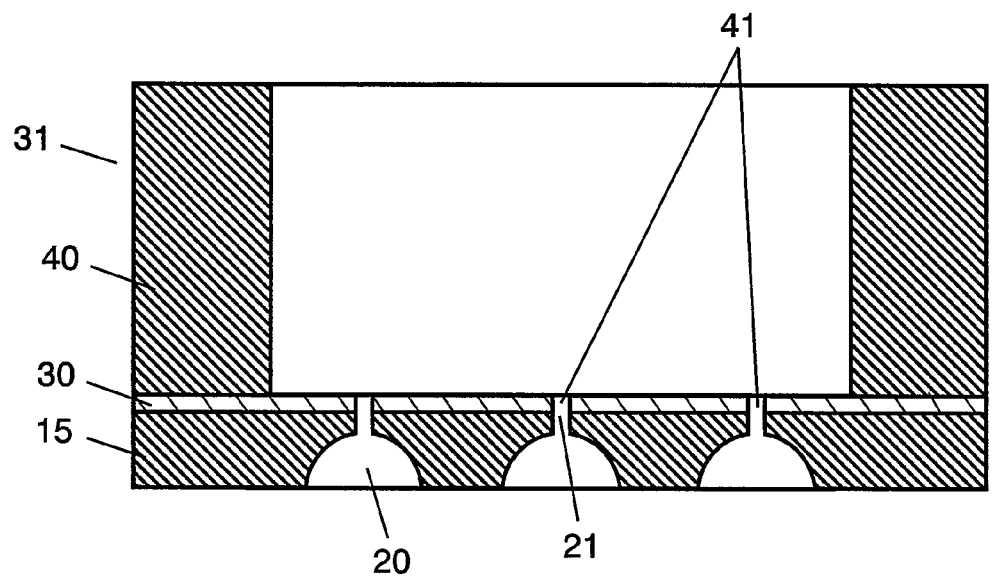
FIG. 25 is a sectional view showing a chip in a device for measuring cellular potential in accordance with a sixth exemplary embodiment of the present invention.
Figure 26:
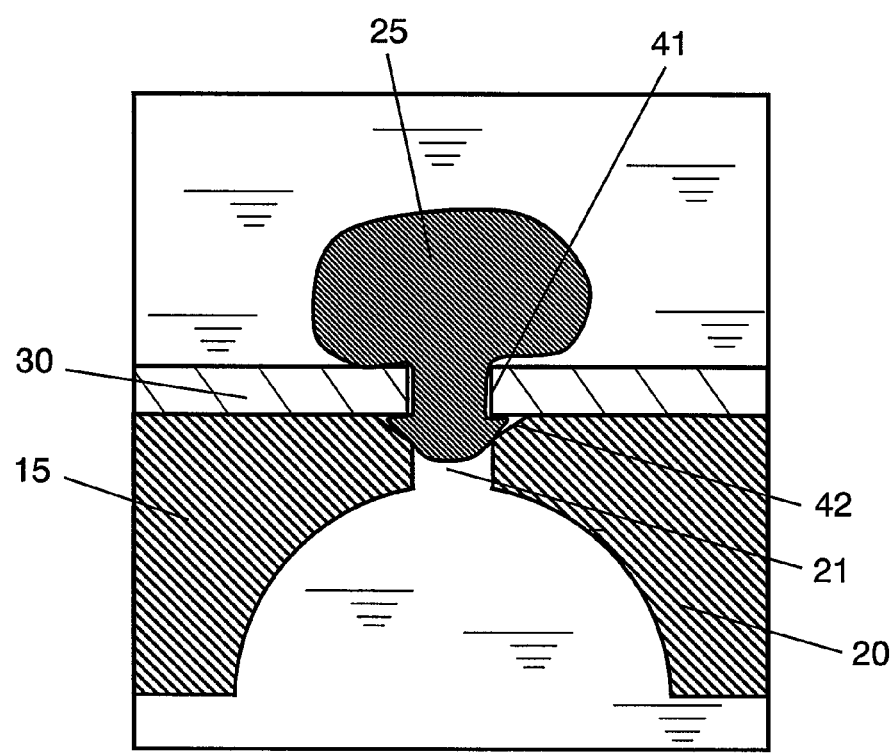
FIG. 26 is an enlarged sectional view showing the chip shown in FIG. 25.

FIG. 25 is a sectional view showing a chip in a device for measuring cellular potential in accordance with a sixth exemplary embodiment of the present invention. FIG. 26 is an enlarged sectional view of the chip shown in FIG. 25. This exemplary embodiment is different from the third exemplary embodiment in that chip 31 is inverted upside down and disposed on chip plate 13 of FIG. 1 and that silicon oxide layer 30 is formed on the upper surface (second surface) of substrate 15.

In other words, chip 31 has substrate 15 having a thickness of about 20 μm, silicon oxide layer 30 having a thickness of about 2 μm, and upper silicon layer 40 having a thickness of about 400 to 500 μm. Silicon oxide layer 30 is disposed on the upper surface of substrate 15. Upper silicon layer 40 is formed on silicon oxide layer 30. Thus, this exemplary embodiment has a configuration combining the third exemplary embodiment and the fifth exemplary embodiment.

Also in this configuration, similar to the third exemplary embodiment, silicon oxide layer 30 becomes an etching stop layer and the thickness of substrate 15 can be designed with high degree of accuracy. Furthermore, the depth of depression 20 can be designed with high degree of accuracy similar to the first exemplary embodiment. As a result, the controlling accuracy of the length of through-hole 21 is improved. In addition, the same effect as that of the fifth exemplary embodiment can be obtained.

Furthermore, in this exemplary embodiment, through-hole 21 is formed in substrate 15 from depression 20 to silicon oxide layer 30, then hole 41 is formed in silicon oxide layer 30. Therefore, an etching gas (for example, $SF_5^+$) for forming through-hole 21 in substrate 15 stops on silicon oxide layer 30 and plus ions of this etching gas are repulsing and dispersing in the lateral direction of through-hole 21. Thus, the etching is allowed to proceed in the lateral direction intentionally.

As a result, as shown in FIG. 26, on the contact surface between substrate 15 and silicon oxide layer 30, the opening diameter of through-hole 21 becomes larger than that of hole 41 of silicon oxide layer 30, so that dent 42 is provided on the inner wall of through-hole 21. Cell 25 that is in close contact with the opening of hole 41 is trapped by dent 42. Thus, adhesiveness between opening of hole 41 and cell 25 is improved. Also in this exemplary embodiment, silicon plate with (110) plane orientation may be used as substrate 15.

Furthermore, in the first to sixth exemplary embodiments, as substrate 15, a silicon plate is used. However, besides, a single crystal plate having a diamond structure, for example, diamond may be used. In addition, the effect of forming depression 20 or depression 20A and through-hole 5 using one resist mask can be obtained when the substrate does not have a diamond structure with (100) plane orientation nor a diamond structure with (110) plane orientation. In the case of using a diamond, as an etching gas, oxygen and the like can be used. Furthermore, chips 22 and 31 have side wall 22A standing from the lower surface of substrate 15 or lower silicon layer 32. However, only substrate 15 may be fixed to the opening of chip plate 13.

Figure 27:
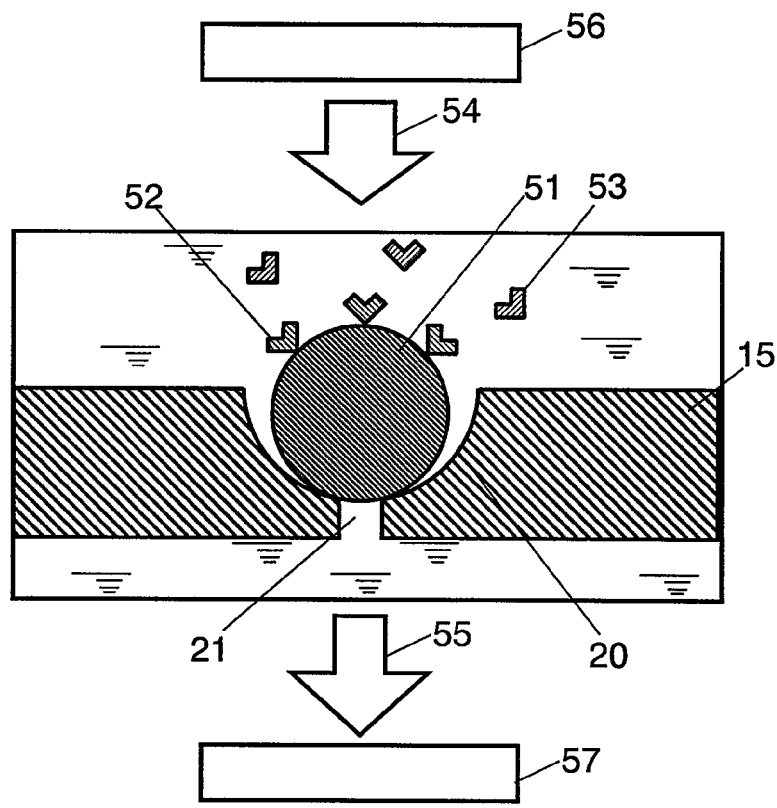
FIG. 27 is a schematic sectional view showing a chemical substance-identification sensor in accordance with another exemplary embodiment of the present invention.

Furthermore, such a diaphragm can be used as a chemical substance-identification sensor for measuring, for example, protein in a solution. FIG. 27 is a schematic sectional view showing a chemical substance-identification sensor in accordance with another exemplary embodiment of the present invention.

With this chemical substance-identification sensor, bead 51 onto which probe 52 adsorbs can be captured in depression 20. Then, probe 52 and protein 53 to be targeted are hybridized in a solution. At this time, probe 52 is modified with a fluorescent material. When bead 51 is then irradiated with light 54 from light source 56, passed light 55 passing through bead 51 is changed due to the hybridization. Therefore, by detecting the change of passed light 55 by detector 57, it is possible to determine whether or not protein 53 to be targeted is present in a solution.

Figure 28:
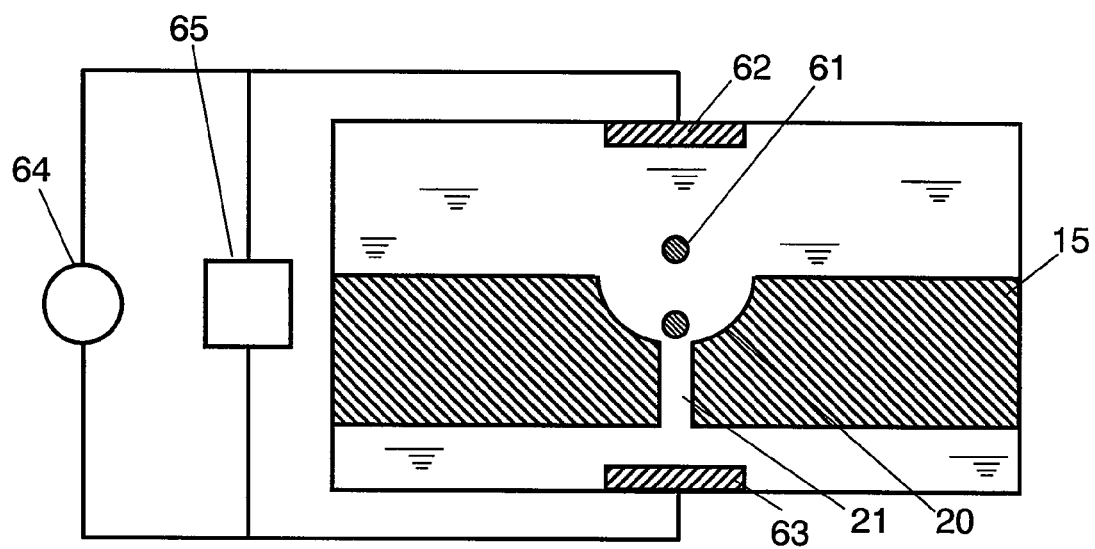
FIG. 28 is a schematic sectional view showing a particle counter in accordance with another exemplary embodiment of the present invention.
Figure 29:
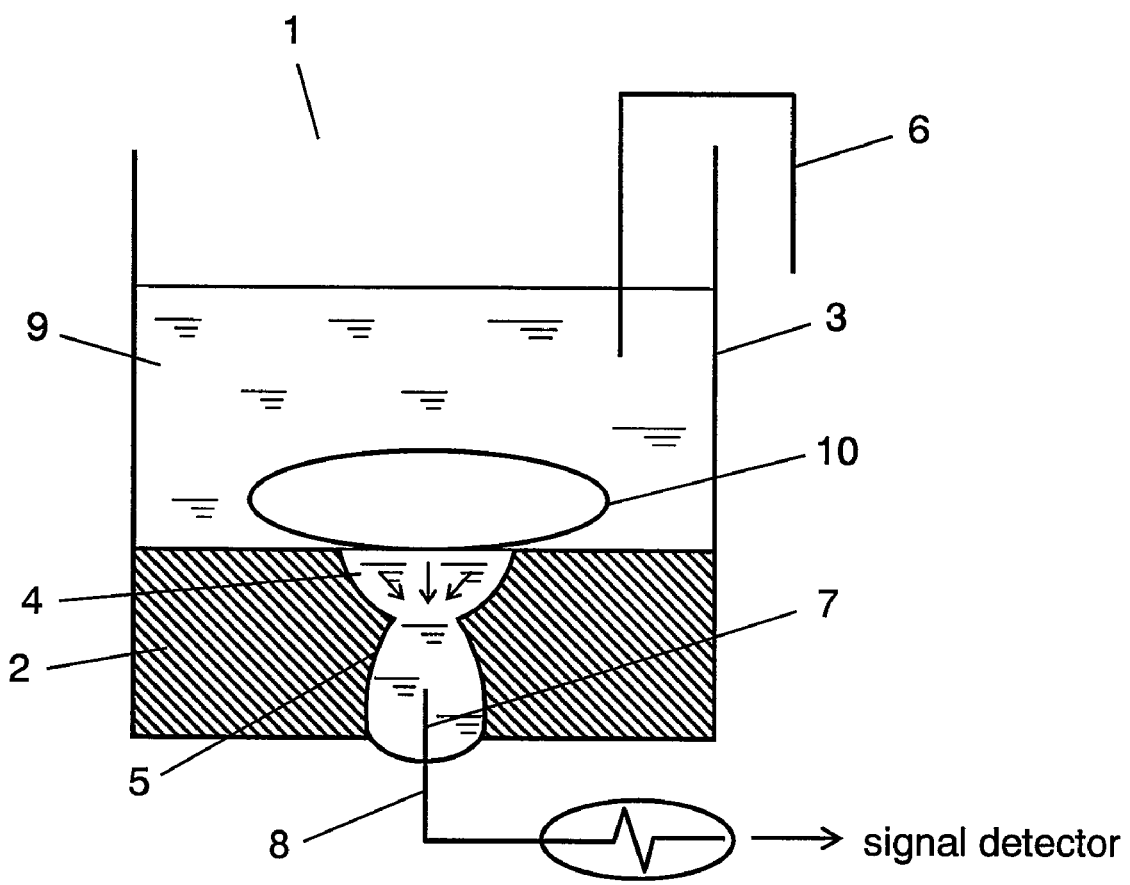
FIG. 29 is a sectional view showing a conventional device for measuring cellular potential.

Furthermore, such a diaphragm can be used as a particle counter. FIG. 28 is a schematic sectional view showing a particle counter in accordance with another exemplary embodiment of the present invention.

This particle counter includes substrate 15, electrodes 62 and 63, power source 64 for allowing electric current to flow between electrodes 62 and 63, and detector 65 for detecting voltage between electrodes 62 and 63.

For example, power source 64 allows a constant current to flow between electrodes 62 and 63 in the presence of an electrolyte. In this state, particles 61 are allowed to pass through through-hole 21. The change of the voltage at this time is measured by detector 65. When particle 61 pass through through-hole 21, the resistance value inside through-hole 21 is changed, which can be measured as the change of voltage.

When particle 61 passes through through-hole 21 from a direction different from the axial direction of through-hole 21, a measurement error may occur. However, when substrate 15 provided with depression 20 and through-hole 21 linked thereto is used, since particles 61 pass through straightly through-hole 21, measurement errors can be reduced.

The diaphragm and the method of manufacturing the same in accordance with the present invention can manage the length of the through-hole. Thus, the length of the through-hole can be equalized at high degree of accuracy. Furthermore, the shape of the surface of the inner wall of the depression that is provided in the substrate and holds cells is made smooth. Furthermore, since the depression and the through-hole are formed by using one resist mask, the positions of the through-holes can be controlled and a plurality of pairs of depressions and through-holes can be formed in substantially the same shape. Thus, the measurement accuracy of a device for measuring cellular potential using this diaphragm can be improved. Accordingly, in the medical and biotechnological fields requiring highly accurate measurement, the device of the present invention is useful in a device in which a fine electronics mechanical system (MEMS) technology is applied.

What is claimed is:

1. A manufacturing method of a diaphragm, comprising:
forming a resist mask having a mask hole on a first surface of a substrate, the substrate including the first surface and a second surface opposite the first surface;
forming a depression on the first surface by isotropic dry etching while the resist mask is maintained; and
forming a through-hole by allowing the through-hole to penetrate the substrate from the depression to the second surface by anisotropic dry etching while the resist mask is maintained,
wherein the opening diameter of the mask hole of the resist mask is substantially the same as that of the through-hole.

2. The manufacturing method of a diaphragm according to claim 1, wherein the depression has a hemispherical shape or a semi-elliptical spherical shape.

3. The manufacturing method of a diaphragm according to claim 1, wherein the substrate is a single crystal plate having any one of a diamond structure with (100) plane orientation and a diamond structure with (110) plane orientation.

4. The manufacturing method of a diaphragm according to claim 1, wherein the opening diameter of the mask hole is more than 0 μm and not more than 3 μm.

5. The manufacturing method of a diaphragm according to claim 1, wherein in the forming of the depression, an etching gas is used, and filling and removing of the etching gas from an etching chamber are repeated a plurality of times.

6. The manufacturing method of a diaphragm according to claim 1, wherein in the forming of the through-hole, an etching gas and an etching suppressing gas are used alternately.

7. The manufacturing method of a diaphragm according to claim 1, further comprising:
preparing the substrate by etching a plate-shaped material having an etching stop layer inside thereof so as to control a thickness of the substrate, before the forming of the resist mask.

8. The manufacturing method of a diaphragm according to claim 7, wherein in the preparing the substrate, a frame body is formed on the etching stop layer by etching the plate-shaped material.

* * * * *